US009758625B2

(12) United States Patent
Bartholomew et al.

(10) Patent No.: US 9,758,625 B2
(45) Date of Patent: Sep. 12, 2017

(54) POLYMERIC BODIPY DYES AND METHODS FOR USING THE SAME

(71) Applicant: Becton, Dickinson and Company, Franklin Lakes, NJ (US)

(72) Inventors: Glenn P. Bartholomew, Escondido, CA (US); Brent S. Gaylord, San Diego, CA (US); Lucy Zhao, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/059,181

(22) Filed: Mar. 2, 2016

(65) Prior Publication Data

US 2016/0264737 A1    Sep. 15, 2016

Related U.S. Application Data

(60) Provisional application No. 62/132,446, filed on Mar. 12, 2015.

(51) Int. Cl.
| | | |
|---|---|---|
| C08G 64/00 | (2006.01) | |
| C08G 79/08 | (2006.01) | |
| G01N 33/58 | (2006.01) | |
| C08G 63/02 | (2006.01) | |

(52) U.S. Cl.
CPC ........... *C08G 79/08* (2013.01); *G01N 33/582* (2013.01)

(58) Field of Classification Search
CPC .................................................... C08G 79/08
USPC ....................................................... 528/219
See application file for complete search history.

(56) References Cited

U.S. PATENT DOCUMENTS

| | | |
|---|---|---|
| 8,575,303 B2 | 11/2013 | Gaylord et al. |
| 8,802,450 B2 | 8/2014 | Gaylord et al. |
| 2003/0220502 A1 | 11/2003 | Waggoner et al. |
| 2004/0142344 A1 | 7/2004 | Bazan et al. |
| 2008/0064042 A1 | 3/2008 | Bazan et al. |
| 2008/0293164 A1 | 11/2008 | Gaylord et al. |
| 2008/0311041 A1* | 12/2008 | Verkman ............... C07D 498/08 424/9.1 |
| 2009/0233373 A1 | 9/2009 | Hamachi et al. |
| 2009/0258434 A1 | 10/2009 | Nagano et al. |
| 2010/0136702 A1 | 6/2010 | Bazan et al. |
| 2010/0197030 A1 | 8/2010 | Mao et al. |
| 2011/0256549 A1 | 10/2011 | Gaylord et al. |
| 2012/0009615 A1 | 1/2012 | Ulrich et al. |
| 2012/0028828 A1 | 2/2012 | Gaylord et al. |
| 2012/0070382 A1 | 3/2012 | Liu |
| 2012/0252986 A1 | 10/2012 | Liu et al. |
| 2013/0190193 A1 | 7/2013 | Bazan et al. |

FOREIGN PATENT DOCUMENTS

| | | |
|---|---|---|
| WO | WO 2010/075514 A1 | 7/2010 |
| WO | WO 2013/101902 A2 | 7/2013 |

OTHER PUBLICATIONS

Alemdaroglu et al. "Poly(BODIPY)s: A New Class of Tunable Polymeric Dyes, Macromolecules", vol. 42, Aug. 13, 2009, pp. 6529-6536.
Chong et al. "Conjugated Polymer anoparticles for Light-Activated Anticancer and Antibacterial Activity with Imaging Capability", Langmuir 2012, 28, 2091-2098.
Donuru et al. "Deep-Red Emissive Conjugated Poly(2,6-BODIPYEthynylene)s Bearing Alkyl Side Chains", Journal of Polymer Science: Part A: Polymer Chemistry, vol. 47, 5354-5366 (2009).
Donuru et al. "Near-infrared emissive BODIPY polymeric and copolyrneric dyes", Polymer, 2010, 51, 5359-5367.
Donuru et al. "Synthesis and Optical Properties of Red and Deep-Red Emissive Polymer and Copolymeric BODIPY Dyes", Chem. Mater. 2009, 21, 2130-2138.
Feng et al. "Water-soluble fluorescent conjugated polymers and their interactions with biomacromolecules for sensitive biosensors", Chem. Soc. Rev., 2010, 39, 2411-2419.
Kim et al. Bodipy-backboned polymers as electron donor in bulk heterojunction solar cells, Chem. Commun., vol. 46, Apr. 13, 2010, pp. 4148-4150.
Liras et al. Conjugated Microporous Polymers Incorporating BODIPY Moieties as Light-Emitting Materials and Recyclable Visible-Light Photocatalysts, Macromolecules, vol. 49, Feb. 17, 2016, pp. 1666-1673.
Loudet et al. "BODIPY Dyes and Their Derivatives: Syntheses and Spectroscopic Properties", Chem. Rev. 2007, 107 (11): 4891-4932.
Meng et al. "Color Tuning of Polyfluorene Emission with BODIPY Monomers", Macromolecules 2009, 42, 1995-2001.
Mula et al. "Dual Bodipy fluorophores linked by polyethyleneglycol spacers", Tet. Lett. 2009, 50, 6383-6388.
Rong et al. "Multicolor Fluorescent Semiconducting Polymer Dots with Narrow Emissions and High Brightness", ACS Nano 2013, 7, 376-384.
Traina et al. "Design and Synthesis of Monofunctionalized, Water-Soluble Conjugated Polymers for Biosensing and Imaging Applications", J. Am. Chem. Soc., 2011, 133 (32) 12600-12607.
Vegesna et al. "Highly Water-Soluble BODIPY-Based Fluorescent Probe for Sensitive and Selective Detection of Nitric Oxide in Living Cells", ACS Appl. Mater. Interfaces 2013, 5, 4107-4112.

(Continued)

*Primary Examiner* — Terressa Boykin
(74) *Attorney, Agent, or Firm* — Glenn J. Foulds; Bret E. Field; Bozicevic, Field & Francis LLP

(57) ABSTRACT

Polymeric BODIPY dyes including light harvesting BODIPY unit-comprising multichromophores are provided. In some embodiments, the dyes are polymeric tandem dyes that include a light harvesting BODIPY unit-comprising multichromophore and an acceptor chromophore covalently linked to the multichromophore in energy-receiving proximity therewith. The polymeric tandem dyes may be covalently linked to a specific binding member. Also provided are methods of evaluating a sample for the presence of a target analyte and methods of labelling a target molecule using compositions including the polymeric tandem dyes. Kits and systems for practicing the subject methods are also provided.

20 Claims, 2 Drawing Sheets

(56) References Cited

OTHER PUBLICATIONS

Wu et al. "Synthesis and Characterization of Near-infrared Emissive BODIPY Based Conjugated Polymers", Synlett 2012, 23, pp. 778-782 and Supporting Information (14 pages).

Yeo et al. "Effective Light-Harvesting Antennae Based on BODIPY-Tethered Cardo Polyfluorenes via Rapid Energy Transferring and Low Concentration Quenching", Macromolecules 2013, 46, pp. 2599-2605.

Zhu et al. "Efficient Tuning Nonlinear Optical Properties: Synthesis and Characterization of a Series of Novel Poly(aryleneethynylene)s Co-Containing BODIPY", Journal of Polymer Science Part A: Polymer Chemistry, vol. 46, Issue 22, pp. 7401-7410, Nov. 15, 2008.

Zhu et al. "Highly Water-soluble Neutral BODIPY Dyes with Controllable Fluorescence Quantum Yields", Org Lett, Feb. 4, 2011; 13(3): 438-441.

Zhu et al. "Highly water-soluble, near-infrared emissive BODIPY polymeric dye bearing RGD peptide residues for cancer imaging," Anal, Chim. Acta 2013, 758, pp. 138-144.

Zhu et al. "Highly water-soluble neutral near-infrared emissive BODIPY polymeric dyes", J. Mater. Chem. 2012, 22, pp. 2781-2790.

* cited by examiner

POLYMERIC BODIPY DYES AND METHODS FOR USING THE SAME

CROSS-REFERENCE TO RELATED APPLICATIONS

Pursuant to 35 U.S.C. §119 (e), this application claims priority to the filing date of U.S. Provisional Patent Application Ser. No. 62/132,446, filed Mar. 12, 2015, the disclosure of which application is incorporated herein by reference.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g. in diagnostic kits, in microscopy or in drug screening. Fluorescent dyes are characterized by a number of parameters allowing a user to select a suitable dye depending on the desired purpose. Parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence and/or to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a fluorescent dye.

SUMMARY

Polymeric BODIPY dyes including light harvesting BODIPY unit-comprising multichromophores are provided. In some embodiments, the dyes are polymeric tandem dyes that include a light harvesting BODIPY unit-comprising multichromophore and an acceptor chromophore covalently linked to the multichromophore in energy-receiving proximity therewith. The polymeric tandem dyes may be covalently linked to a specific binding member. Also provided are methods of evaluating a sample for the presence of a target analyte and methods of labelling a target molecule using compositions including the polymeric tandem dyes. Kits and systems for practicing the subject methods are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
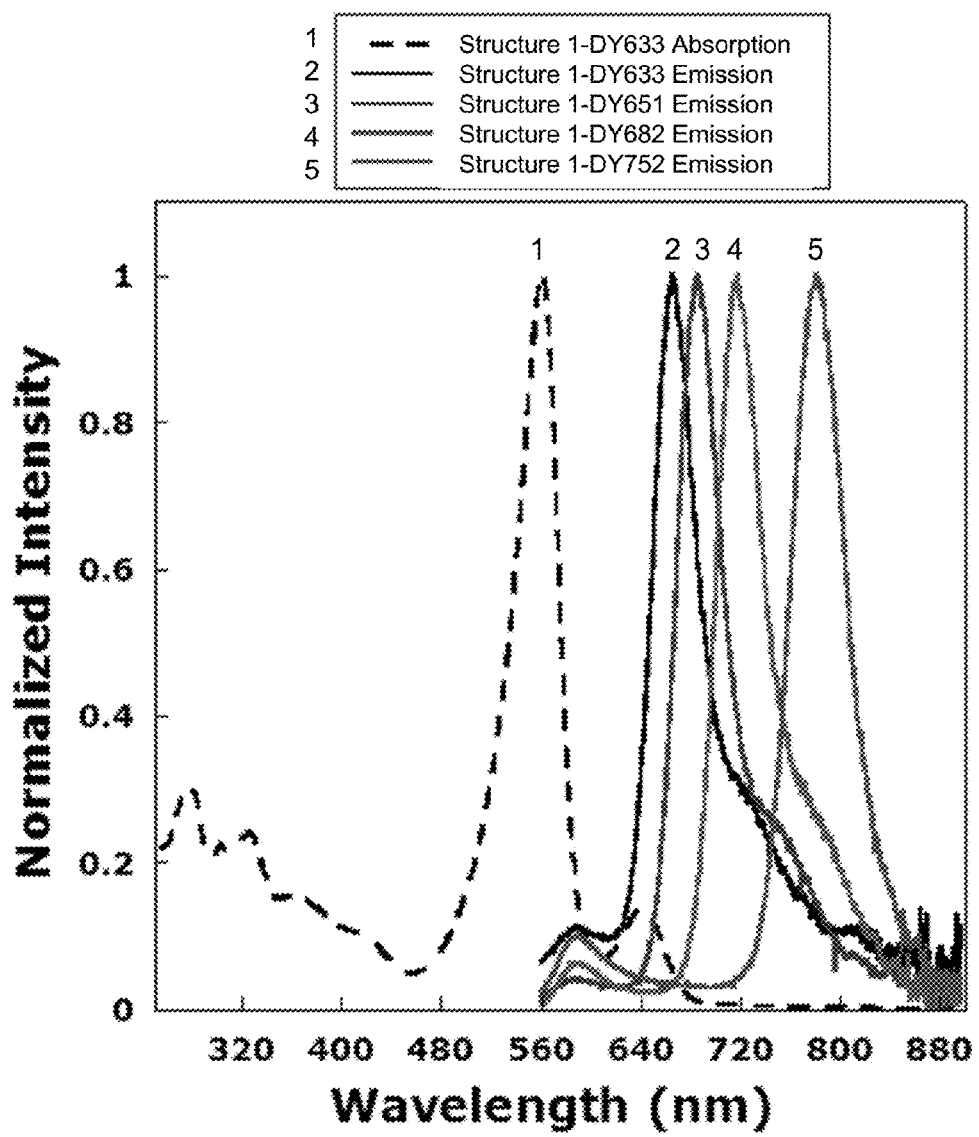
FIG. 1 illustrates absorption and emission of exemplary polymeric tandem dyes with a variety of acceptor dyes attached at the internal linker site. No specific binding member is attached for these structures.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

As used herein, the terms "affinity" and "avidity" have the same meaning and may be used interchangeably herein.

"Affinity" refers to the strength of binding, increased binding affinity being correlated with a lower Kd.

As used herein, the terms "determining," "measuring," and "assessing," and "assaying" are used interchangeably and include both quantitative and qualitative determinations.

As used herein, the terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g. a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

As used herein, the term "biomolecule" refers to an organic molecule or macromolecule of a naturally occurring class of molecules, or a derivative thereof. Biomolecule is meant to encompass polypeptides (e.g., a peptide, an antibody or an antibody fragment), polynucleotides, carbohydrates (e.g., sugars) and lipids. In some cases, the biomolecule is a specific binding member (e.g., as described herein).

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein, the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

The term "separating", as used herein, refers to physical separation of two elements (e.g., by size or affinity, etc.) as well as degradation of one element, leaving the other intact.

As used herein, the term "specific binding" refers to the ability of a capture agent (or a first member of a specific binding pair) to preferentially bind to a particular analyte (or a second member of a specific binding pair) that is present, e.g., in a homogeneous mixture of different analytes. In some instances, a specific binding interaction will discriminate between desirable and undesirable analytes in a sample with a specificity of 10-fold or more for a desirable analyte over an undesirable analytes, such as 100-fold or more, or 1000-fold or more. In some cases, the affinity between a capture agent and analyte when they are specifically bound in a capture agent/analyte complex is at least $10^{-8}$M, at least $10^{-9}$M, such as up to $10^{-10}$M.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "polyethylene oxide", "PEO", "polyethylene glycol", "PEG" and "PEG moiety" are used interchangeably and refer to a polymeric group including a chain described by the formula $-(CH_2-CH_2-O-)_n-$ or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

As used herein, the terms "chemoselective functional group", "chemoselective tag" and "conjugation tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), as well as hydroxyl, hydrazido, hydrazino, aldehyde, ketone, azido, alkyne, phosphine, epoxide, and the like. In some cases, the chemoselective functional group is a protected functional group that must be deprotected prior to covalent linking. In certain instances, the chemoselective functional group is may be activated prior to or during covalent linking with a compatible functional group.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

The term "alkaryl" or "aralkyl" refers to the groups -alkylene-aryl and substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$), (O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S) OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^6$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

Other definitions of terms may appear throughout the specification.

DETAILED DESCRIPTION

As summarized above, polymeric tandem dyes are provided. In some embodiments, the polymeric tandem dyes include a light harvesting BODIPY unit-comprising multichromophore and an acceptor chromophore covalently linked to the multichromophore in energy-receiving proximity therewith. The polymeric tandem dyes may be covalently linked to a specific binding member. Also provided are methods of evaluating a sample for the presence of a target analyte and methods of labelling a target molecule using compositions including the polymeric tandem dyes. Kits and systems for practicing the subject methods are also provided.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, polymeric dyes and tandem dyes including an acceptor chromophore are described first in greater detail. Next, conjugates which include the polymeric dyes are described. Then, methods of interest in which compositions including the subject polymeric tandem dyes find use are reviewed. Systems and kits that may be used in practicing methods of the invention are also described.

Light Harvesting BODIPY Unit-Comprising Multichromophores

As summarized above, the present disclosure provides a polymeric BODIPY dye. In some embodiments, the polymeric dye includes a light harvesting BODIPY unit-comprising multichromophore. In some embodiments, the multichromophore is itself fluorescent. In certain instances, the multichromophore is a polymeric tandem dye. As such, in some embodiments, the multichromophore further includes an acceptor chromophore covalently linked to the multichromophore in energy-receiving proximity therewith.

As used herein the terms, "light harvesting multichromophore", "polymeric dye" and "conjugated polymer" are used interchangeably and refer to a conjugated polymer which has a structure capable of harvesting light with a particular absorption maximum wavelength and converting it to emitted light at a longer emission maximum wavelength. In some cases, the light harvesting multichromophore is itself fluorescent. Conjugated polymers (CPs) are characterized by a delocalized electronic structure and may have an effective conjugation length that is substantially shorter than the length of the polymer chain, because the backbone may contain a large number of conjugated segments in close proximity. In some cases, conjugated polymers are efficient for light harvesting and provide for optical amplification via Forster energy transfer to an acceptor. In some embodiments, the conjugated polymer includes a plurality of first optically active units forming a conjugated system, having an absorption wavelength (e.g., as described herein) at which the first optically active units absorbs light to form an excited state. In certain instances, the polymeric dye includes a conjugated polymer segment or an oligomeric structure including bandgap-lowering n-conjugated repeat units.

As used herein the term "unit" refers to a structural subunit of a polymer. The term unit is meant to include monomers, co-monomers, co-blocks, conjugated segments, repeating units, and the like. A "repeating unit" is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer, each block may define a distinct repeating unit. In some cases, a repeating unit of the polymer includes a single monomer group. In certain instances, a repeating unit of the polymer includes two or more monomer groups, i.e., co-monomer groups, such as two, three, four or more co-monomer groups. As used herein, the term "co-monomer" or "co-monomer group" refers to a structural unit of a polymer that may itself be part of a repeating unit of the polymer. In some embodiments, the conjugated polymer includes a block copolymer that is composed of blocks of polymerized monomers. In such cases, the block copolymer may be described as having distinct repeating units each corresponding to a distinct co-block of the polymer. In some cases, the polymer is a diblock copolymer that contains two different co-blocks. In such cases, the polymer may be described as including co-blocks, where each co-block may be composed of co-monomers, such as one, two, three or more co-monomers.

As used herein, the term "BODIPY unit" refers to a structural subunit of the multichromophore which includes a chromophore having the following boron-dipyrromethene (BODIPY) core structure:

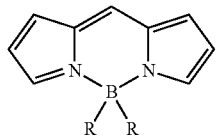

where each R is independently selected from the group consisting of F, OH, H, alkyl, substituted alkyl, aryl, substituted aryl, heteroaryl, substituted heteroaryl, alkoxy, substituted alkoxy, alkynyl and substituted alkynyl. The BODIPY core structure may be linked to adjacent units of the multichromophore via any convenient positions of the core structure, and may be further optionally substituted. In some instances, the BODIPY unit is capable of π conjugation to adjacent units of the polymer. In some embodiments, the BODIPY unit defines a repeating unit. In certain embodiments, the BODIPY unit defines a co-monomer which is part of a repeating unit. Any convenient BODIPY-containing structures may be adapted for use in the subject multichromophores as a BODIPY unit. BODIPY-containing structures of interest include, but are not limited to, those BODIPY dyes and derivatives described by Loudet and Burgess in "BODIPY Dyes and Their Derivatives: Syntheses and Spectroscopic Properties", Chem. Rev. 2007, 107 (11): 4891-4932.

In certain embodiments, the BODIPY unit is described by the structure:

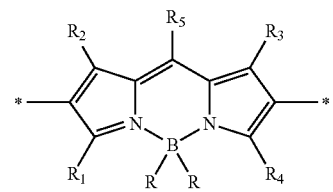

where:
$R^1$, $R^2$, $R^3$ and $R^4$ are each independently selected from H, an alkyl or a substituted alkyl;
$R^5$ is an alkyl, a substituted alkyl, an aryl, a substituted aryl, a heteroaryl, a substituted heteroaryl, wherein $R^5$ is optionally substituted with a water solubilizing group; and
each R is selected from the group consisting of F, OH, H, alkyl, substituted alkyl, aryl, substituted aryl, heteroaryl, substituted heteroaryl, alkoxy, substituted alkoxy, alkynyl and substituted alkynyl.

Any convenient light harvesting multichromophores may be adapted to include a BODIPY unit. Light harvesting multichromophores of interest that may be modified to include a BODIPY unit include, but are not limited to, those dyes described by Gaylord et al. in US Publication Nos. 20040142344, 20080293164, 20080064042, 20100136702, 20110256549, 20120028828, 20120252986 and 20130190193 and U.S. Pat. Nos. 8,575,303 and 8,802450, the disclosures of which Publications and Patents are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

The subject multichromophore may be water soluble. Any convenient water solubilizing groups may be included in the multichromophore to provide for increased water-solubility of the dye. While the increase in solubility may vary, in some instances the increase (as compared to the compound without the WSG(s)) is 2 fold or more, e.g., 5 fold, 10 fold, 25 fold, 50 fold, 100 fold or more. The term "water solubilizing group" (WSG) refers to a group that is well solvated in aqueous environments e.g., under physiological conditions, and that imparts improved water solubility to the molecules to which it is attached. In some embodiments, a WSG increases the solubility of the multichromophore in a predominantly aqueous solution, as compared to a multichromophore which lacks the WSG. The water soluble groups may be any convenient hydrophilic group that is well solvated in aqueous environments. In some cases, the hydrophilic water soluble group is charged, e.g., positively or negatively charged. In certain cases, the hydrophilic water soluble group is a neutral hydrophilic group. In some embodiments, the WSG is a hydrophilic polymer, e.g., a polyethylene glycol, a cellulose, a chitosan, or a derivative thereof. Water soluble groups of interest include, but are not limited to, carboxylate, phosphonate, phosphate, sulfonate, sulfate, sulfinate, sulfonium, ester, polyethylene glycols (PEG) and modified PEGs, hydroxyl, amine, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{ZZ}$, and R$^{ZZ}$ and R$^{YY}$ are independently selected from H and C$_{1-3}$ alkyl.

Multiple WSGs may be included at a single location in the subject multichoromophores via a branching linker. Any convenient branching linkers may be utilized in order to provide for linking to multiple WSG. Branching linkers of interest include, but are not limited, tertiary amino groups (e.g., where N is a branching atom), amino acid residues, substituted aryl groups, substituted heteroaryl groups, substituted heterocyclic groups, dendrimers, and the like. In certain embodiments, the branching linker is an aralkyl substituent that is further disubstituted with water soluble group(s). As such, in some cases, the branching linker group is a substituent of the multichromophore that connects the multichromophore to two or more water soluble groups. In some cases, the incorporation of multiple WSGs via branching linkers imparts a desirable solubility on the multichromophore. In some embodiments, the multichromophore includes substituent(s) selected from the group consisting of an alkyl, an aralkyl and a heterocyclic group, each group further substituted with a water solubilizing group. In certain cases, the WSG is a hydrophilic polymer group, such as a polyethylglycol (PEG) (e.g., a PEG of 2-20 units).

The multichromophore may be of any convenient length. In some cases, the particular number of monomeric repeating units or segments of the multichromophore may fall within the range of 2 to 500,000, such as 2 to 100,000, 2 to 30,000, 2 to 10,000, 2 to 3,000 or 2 to 1,000 units or segments, or such as 5 to 100,000, 10 to 100,000, 100 to 100,000, 200 to 100,000, or 500 to 50,000 units or segments. In some instances, the particular number of monomeric repeating units or segments of the multichromophore may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments.

The multichromophore may be of any convenient molecular weight (MW). In some cases, the MW of the multichromophore may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000.

In some embodiments, the BODIPY unit constitutes 25% or more by molarity of the multichromophore, such as 30% or more, 40% or more, 45% or more, 50% or more, 60% or more, 70% or more, or even more by molarity of the multichromophore. In such cases, the multichromophore may include 5 or more repeating units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more repeating units. In such cases, the multichromophore may include 5 or more co-monomer units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more co-monomer units.

The subject multichromophore may have one or more desirable spectroscopic properties, such as a particular absorption maximum wavelength, a particular emission maximum wavelength, extinction coefficient, quantum yield, narrow band spectral features, low energy absorption bands, and the like.

In certain embodiments, the multichromophore has narrow band spectral features. A narrow band spectral feature refers to an absorbance or emission spectra with a full width at half maximum (FWHM) of 50 nm or less with peaks centered at 500 nm or more. In some embodiments, the dye has low energy absorption bands having a bandwidth of 200 nm or less, such as 150 nm or less, 100 nm or less, 90 nm or less, 80 nm or less, 70 nm or less, 60 nm or less, 50 nm or less, 40 nm or less, 30 nm or less, 20 nm or less, or even less. In some cases, the bandwidth is determined via a full width at half maximum (FWHM) measurement. In certain embodiments, the dye has low energy absorption bands having a bandwidth of 50 nm or less.

In some embodiments, the multichromophore has an absorption maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of absorption maxima of interest include, but are not limited to: 590 nm, 630 nm, 650 nm, 680 nm and 750 nm. In certain embodiments, the multichromophore has an absorption maximum wavelength of 590 nm±5 nm, 630 nm±5 nm, 650 nm±5 nm, 680 nm±5 nm or 750 nm±5 nm. In some embodiments, the multichromophore has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of interest include, but are not limited to: 605 nm, 650 nm, 680 nm, 700 nm and 805 nm. In certain embodiments, the multichromophore has an emission maximum wavelength of 605 nm±5 nm, 650 nm±5 nm, 680 nm±5 nm, 700 nm±5 nm or 805 nm±5 nm.

In some instances, the multichromophore has an extinction coefficient of $5 \times 10^5$ cm$^{-1}$M$^{-1}$ or more, such as $6 \times 10^5$ cm$^{-1}$M$^{-1}$ or more, $7 \times 10^5$ cm$^{-1}$M$^{-1}$ or more, $8 \times 10^5$ cm$^{-1}$M$^{-1}$ or more, $9 \times 10^5$ cm$^{-1}$M$^{-1}$ or more, such as $1 \times 10^6$ cm$^{-1}$M$^{-1}$ or more, $1.5 \times 10^6$ cm$^{-1}$M$^{-1}$ or more, $2 \times 10^6$ cm$^{-1}$M$^{-1}$ or more, $2.5 \times 10^6$ cm$^{-1}$M$^{-1}$ or more, $3 \times 10^6$ cm$^{-1}$M$^{-1}$ or more, $4 \times 10^6$ cm$^{-1}$M$^{-1}$ or more, $5 \times 10^6$ cm$^{-1}$M$^{-1}$ or more, $6 \times 10^6$ cm$^{-1}$M$^{-1}$ or more, $7 \times 10^6$ cm$^{-1}$M$^{-1}$ or more, or $8 \times 10^6$ cm$^{-1}$M$^{-1}$ or more. In such cases, the multichromophore may have 5 or more repeating units, such as 6 or more, 7 or more, 8 or more, 9 or more, 10 or more, or even more repeating units. In some embodiments, the multichromophore has a molar extinction coefficient of $5 \times 10^5$ M$^{-1}$ cm$^{-1}$ or more. In certain embodiments, the multichromophore has a molar extinction coefficient of $1 \times 10^6$ M$^{-1}$ cm$^{-1}$ or more.

In some instances, the multichromophore has an extinction coefficient of 40,000 cm$^{-1}$M$^{-1}$ per co-monomer or more, such as 45,000 cm$^{-1}$M$^{-1}$ per co-monomer or more, 50,000 cm$^{-1}$M$^{-1}$ per co-monomer or more, 55,000 cm$^{-1}$M$^{-1}$ per co-monomer or more, 60,000 cm$^{-1}$M$^{-1}$ per co-monomer or more, 70,000 cm$^{-1}$M$^{-1}$ per co-monomer or more, 80,000 cm$^{-1}$M$^{-1}$ per co-monomer or more, 90,000 cm$^{-1}$M$^{-1}$ per co-monomer or more, 100,000 cm$^{-1}$M$^{-1}$ per co-monomer or more, or even more. In some instances, the multichromophore has an extinction coefficient of 40,000 cm$^{-1}$M$^{-1}$ per repeating unit or more, such as 45,000 cm$^{-1}$M$^{-1}$ per repeating unit or more, 50,000 cm$^{-1}$M$^{-1}$ per repeating unit or more, 55,000 cm$^{-1}$M$^{-1}$ per repeating unit or more, 60,000 cm$^{-1}$M$^{-1}$ per repeating unit or more, 70,000 cm$^{-1}$M$^{-1}$ per repeating unit or more, 80,000 cm$^{-1}$M$^{-1}$ per repeating unit or more, 90,000 cm$^{-1}$M$^{-1}$ per repeating unit or more, 100,000 cm$^{-1}$M$^{-1}$ per repeating unit or more, 100,000 cm$^{-1}$M$^{-1}$ per repeating unit or more, 120,000 cm$^{-1}$M$^{-1}$ per repeating unit or more, or even more. In some instances, the extinction coefficient described herein is an average extinction coefficient. In certain instances, the repeat unit of the multichromophore may include a single monomer, two co-monomers, or three or more co-monomers.

In certain embodiments, the multichromophore has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, 0.6 or more, 0.7 or more, or even more. In certain cases, the multichromophore has a quantum yield of 0.1 or more. In certain instances, the multichromophore has a quantum yield of 0.3 or more.

It is understood that in some cases the multichromophores may include co-blocks (e.g., n and m co-blocks). The subject multichromophores may include any convenient linear arrangements of n and m co-blocks of various lengths within the structure of the overall polymer. In addition, the multichromophores may include any convenient arrangements of co-monomers within such n and/or m co-blocks. A variety of polymer synthesis methods may be utilized to prepare co-monomers and co-blocks of interest in the preparation of the subject multichromophores. It is understood that in some cases, the polymerization methods may produce a composition including a population of conjugated polymers that includes some variation with respect to the particular length and/or end groups (e.g., terminal groups) present in each CP of the population. The formulae depicted herein may refer to a single compound or to a population or sub-population of polymeric compounds.

In some embodiments, the multichromophore includes a BODIPY-comprising conjugated segment described by formula (I):

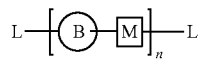

(I)

wherein:
B is a BODIPY unit (e.g., as described herein);
M is a π conjugated co-monomer;
each L is an end group; and
n is an integer of 1 to 100,000. In certain instances of formula (I), each L is independently selected from the group consisting of a terminal group, a π conjugated segment, a linker and a linked specific binding member.

Any convenient π conjugated co-monomers may be utilized in the subject multichromophores. As used herein, the term "π conjugated co-monomer" refers to any convenient monomer subunit of a polymer that is capable of π conjugation (i.e., delocalization of pi electrons across adjacent units) to adjacent groups along a polymer backbone. In certain embodiments of formula (I), M is selected from a fused 6-5-6 tricyclic co-monomer, a fluorene co-monomer, a phenylene-vinylene co-monomer, a phenylene-ethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer. In certain embodiments of formula (I), M is a phenylene-vinylene co-monomer. In some instances of formula (I), M is a phenylene-ethynylene co-monomer. In some cases of formula (I), M is a carbazole co-monomer. In certain instances of formula (I), M is a $C_2$-$C_{12}$ alkyne co-monomer. In certain cases of formula (I), M is a an arylene-ethynylene co-monomer. In some embodiments of formula (I), M is a, a heteroarylene-ethynylene co-monomer. In some instances of formula (I), M is a arylene co-monomer. In some cases of formula (I), M is a heteroarylene co-monomer.

In some embodiments of formula (I), M is a fused 6-5-6 tricyclic co-monomer. A fused 6-5-6 tricyclic co-monomer is a co-monomer including a tricyclic aromatic group having three fused rings in the configuration 6-5-6, i.e. two benzo ring fused to a central 5 membered ring. The 5-membered ring may be a carbocycle or a heterocycle and may further include a sidechain substituent at the ring atom that is not fused to a benzo ring. In certain instances, the fused 6-5-6 tricyclic co-monomer is described by the following structure:

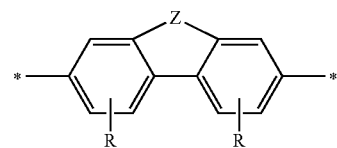

where:
Z is —C(R$^1$)$_2$— or —N(R$^1$)—;
each R is independently H or one or more aryl substituents; and
each R$^1$ is independently selected from the group consisting of an alkyl, a substituted alkyl, an aralkyl, a substituted aralkyl, a PEG moiety and -L$^1$-Z$^1$, where L$^1$ is a linker and Z$^1$ is a chemoslective tag (e.g., a tag including a chemoslective functional group) or a WSG. As used in any of the formulae described herein, * denotes a site for covalent attachment to the unsaturated backbone of a conjugated polymer or an end group. In some embodiments, when Z is —N(R$^1$)—, the fused 6-5-6 tricyclic co-monomer is a carbazole co-monomer. Any convenient carbazole co-monomers may be utilized in the subject multichromophores. In some embodiments, when Z is —C(R$^1$)$_2$—, the fused 6-5-6 tricyclic co-monomer is a fluorene co-monomer. Any convenient fluorene co-monomers may be utilized in the subject multichromophores. In some embodiments of formula (I), M is a carbazole co-monomer. In certain instances of the fused 6-5-6 tricyclic co-monomer, each R$^1$ is selected from a benzyl group substituted with one, two or more PEG moieties or an alkyl group substituted with two or more PEG moieties.

In some embodiments of formula (I), M is a fluorene co-monomer. A fluorene co-monomer is an aromatic group having a 9H-fluorene core structure substituted at the 9 position with any convenient sidechain substituent(s). In some cases, the fluorene co-monomer is a 9,9-disubstituted fluorene. The fluorene co-monomer may be conjugated to adjacent polymeric backbone groups via any convenient positions of the fluorene core structure, such as any two convenient positions selected from positions 1-8 (see numbering scheme below). In some embodiments, the fluorene core structure is linked to adjacent groups of the polymer backbone via the 2- and 7-positions (see numbering scheme below). In certain embodiments, the fluorene co-monomer is described by the following structure:

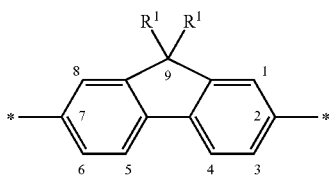

where each $R^1$ is independently selected from an alkyl, a substituted alkyl, an aralkyl, a substituted aralkyl, a PEG moiety and -$L^1$-$Z^1$, where $L^1$ is a linker and $Z^1$ is a chemoselective tag (e.g., a tag including a chemoselective functional group) or a WSG. In certain instances of the fluorene co-monomer, each $R^1$ is selected from a benzyl group substituted with one, two or more PEG moieties or an alkyl group substituted with two or more PEG moieties. In some cases, $Z^1$ includes a functional group that finds use in covalently linking the multichromophore to an acceptor chromophore (e.g., as described herein). In certain instances, $Z^1$ includes an amino group for covalently linking to the acceptor chromophore. In certain instances, $Z^1$ includes a carboxylic acid group, or derivative thereof, for covalently linking to the acceptor chromophore. In certain embodiments, $L^1$ is a branched linker that links to two or more $Z^1$ groups (e.g., WSGs). In certain instances, the fluorene co-monomer is further substituted with a $R^5$ and/or $R^6$ substituent located at one, two or more positions selected from positions 1, 3, 4, 5, 6 and 8, where $R^5$ and $R^6$ are independently selected from a water solubilizing group (WSG) and an aryl substituent (e.g., as described herein).

In some instances, the fluorene co-monomer is described by the structure:

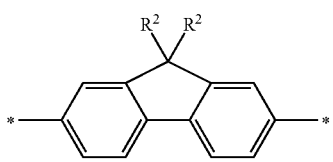

where each $R^2$ is an alkyl substituted with a water soluble group, or a branched linker connected to two or more water soluble groups (e.g., a PEG-disubstituted benzyl or a PEG substituted alkyl). In certain instances of the fluorene co-monomer, each $R^2$ is a benzyl group substituted with one, two or three PEG moieties (e.g., —O(CH$_2$CH$_2$O)$_n$R' where R' is H or an alkyl and n is 1-20, e.g., 3-16 such as n is 8-16). In certain instances of the fluorene co-monomer, each $R^2$ is a benzyl group substituted with one —O(CH$_2$CH$_2$O)$_n$R' group (e.g., at the 2, 3 or 4 position), where R' is H or an alkyl and n is 1-20, e.g., 3-16 such as n is 8-16. In certain instances of the fluorene co-monomer, each $R^2$ is a benzyl group substituted with two —O(CH$_2$CH$_2$O)$_n$R' groups (e.g., at the 2,4-, 3,4- or 3,5-positions), where each R' is independently H or an alkyl and each n is independently 1-20, e.g., 3-16 such as n is 8-16. In certain instances of the fluorene co-monomer, each $R^2$ is a benzyl group substituted with three —O(CH$_2$CH$_2$O)$_n$R' groups (e.g., at the 2,4,6-, 2,4,5- or 3,4,5-positions), where each R' is independently H or an alkyl and each n is independently 1-20, e.g., 3-16 such as n is 8-16. In certain instances of the fluorene co-monomer, each $R^2$ is a lower alkyl group substituted with a trivalent branching group each substituted with two PEG moieties (e.g., a —CO—NR"$_2$ or —O(CH$_2$R")$_2$ trivalent branching group where each R" is independently a PEG moiety (e.g., —O(CH$_2$CH$_2$O)$_n$R' where R' is H or an alkyl and n is 1-20, e.g., 3-16 such as n is 8-16). In certain embodiments, the fluorene co-monomer is described by the following structure:

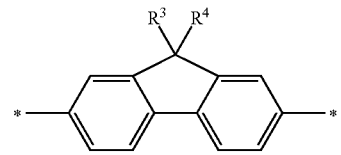

where $R^3$ is an alkyl substituted with a water soluble group (e.g., a PEG substituted alkyl), and $R^4$ is $L^1$-$Z^2$ wherein $L^1$ is a linker and $Z^2$ is a chemoselective tag (e.g., for conjugation to an acceptor chromophore) or an acceptor chromophore. Any convenient chemoselective functional groups may be included in the subject multichromophores, including, but not limited to, carboxylic acid, active ester (e.g., NHS or sulfo-NHS ester), amino, hydroxyl, thiol, maleimide, iodoacetyl, hydrazido, hydrazino, aldehyde, ketone, azido, alkyne, phosphine, epoxide, and the like. In some cases, the chemoselective tag is utilized to covalently link any convenient moieties (e.g., an acceptor chromophore) to the multichromophore. In certain instances, $Z^2$ includes an amino group for covalently linking to an acceptor chromophore. In certain instances, $Z^2$ includes a carboxylic acid group, or derivative thereof, for covalently linking to an acceptor chromophore. In certain instances of the fluorene co-monomer, $R^3$ is a lower alkyl group substituted with a trivalent branching group each substituted with two PEG moieties (e.g., a —CO—NR"$_2$ or —O(CH$_2$R")$_2$ trivalent branching group where each R" is a PEG moiety (e.g., —O(CH$_2$CH$_2$O)$_n$R' where R' is H or an alkyl and n is 1-20, e.g., 3-16 such as n is 8-16).

In some instances, the fluorene co-monomer is described by the following structure:

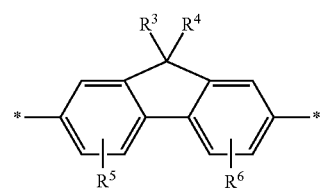

wherein:
$R^3$ is a substituent comprising a water solubilizing group (e.g., as described herein);
$R^4$ is $L^1$-$Z^2$ wherein $L^1$ is a linker and $Z^2$ is a chemoselective tag (e.g., for conjugation to an acceptor chromophore) or an acceptor chromophore; and $R^5$ and $R^6$ are independently selected from H, a water solubilizing group and an aryl substituent (e.g., an alkyl, a substituted alkyl, an alkoxy, a substituted alkoxy, a halogen or a nitro). In certain instances of the fluorene co-monomer, $R^3$ is a lower alkyl group substituted with a trivalent branching group each substituted with two PEG moieties (e.g., a —CO—NR''$_2$ or —O(CH$_2$R'')$_2$ trivalent branching group where each R'' is a PEG moiety (e.g., —O(CH$_2$CH$_2$O)$_n$R' where R' is H or an alkyl and n is 1-20, e.g., 3-16 such as n is 8-16).

Any convenient end groups may be utilized at the terminals of the subject multichromphores. End groups of interest include, but are not limited to a terminal capping group, a π conjugated segment, a linker and a linked specific binding member. In some embodiments, a terminal capping group is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In some embodiments, the terminal capping group is substituted with a linker and/or a conjugation tag to which any convenient moiety, such as a specific binding member, may be linked. In certain cases, the end group is a group derived from a monomer used in the method of polymerization, e.g., a group such as a halogen (e.g., Br), a boronic acid or a boronic ester, which is capable of undergoing further conjugation. In some instances, the end group is a π conjugated segment. As used herein, a π conjugated segment refers to any convenient additional segment of a conjugated polymer to which the multichromophore may be conjugated (i.e., allowing delocalization of pi electron across adjacent units). In certain embodiments, the end unit is a linker, such as a linker including a functional group suitable for conjugation to a specific binding moiety. It is understood that linkers and conjugation tags located at the terminals of the multichromophore may be selected so as to be orthogonal to any other linkers and chemoselective tags that may be present at a sidechain of the multichromophore. As used herein, the terms chemoselective tag and conjugation tag, may be used interchangeably, and refer to any convenient group that includes a functional group of interest (e.g., a chemoselective functional group as described herein). In certain embodiments, an amino functional group or derivative thereof is included at an end group (e.g., $G^1$ and/or $G^2$) and a carboxylic acid functional group or derivative thereof is included at $Z^1$. In certain embodiments, a carboxylic acid functional group or derivative thereof is included at an end group (e.g., $G^1$ and/or $G^2$) and an amino functional group or derivative thereof is included at $Z^1$.

Polymeric Tandem Dyes

As summarized above, the present disclosure provides polymeric tandem dyes that include a light harvesting BODIPY unit-comprising multichromophore. Any of the light harvesting BODIPY unit-comprising multichromophores described herein may be utilized in the subject polymeric tandem dyes. In some embodiments, the polymeric tandem dyes include a light harvesting BODIPY unit-comprising multichromophore and an acceptor chromophore covalently linked to the multichromophore in energy-receiving proximity therewith. In some embodiments, the light harvesting multichromophore is water soluble.

Polymeric tandem dyes include two covalently linked moieties: a donor light harvesting multichromophore (e.g., as described herein) and an acceptor chromophore. As used herein, the term "acceptor chromophore" refers to a light-absorbing molecule that is capable of receiving or absorbing energy transferred from the multichromophore. In some cases, the acceptor chromophore can either emit as light the energy received from the multichromophore or dissipate the energy as heat. It is understood that, unless otherwise stipulated, in the structures and formulae depicted herein, the label "dye" refers to an "acceptor chromophore". In some instances, the acceptor chromophore is a quencher. As used herein, the term "quencher" refers to an acceptor chromophore that absorbs energy from the multichromophore and does not emit light but rather can dissipate the energy as heat. In certain instances, the acceptor chromophore is a fluorescent dye. In some embodiments, the polymeric tandem dye may be excited at the absorption maximum wavelength of the donor multichromophore and may emit light at the emission wavelength of the acceptor chromophore. In some cases, the light-harvesting multichromophore can transfer energy to an acceptor chromophore species in energy-receiving proximity. Mechanisms for energy transfer include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the acceptor chromophore provides for efficient energy transfer. In some instances, under conditions for efficient energy transfer, amplification of the emission from the acceptor chromophore occurs when the number of individual chromophores in the light harvesting multichromophore system is large; that is, the emission from the signaling chromophore is more intense when the incident light (the "pump light") is at a wavelength which is absorbed by the light harvesting multichromophore than when the signaling chromophore is directly excited by the pump light.

In some cases, by "efficient" energy transfer is meant 5% or more of the energy harvested is transferred to the acceptor, such as 10% or more, 20% or more, 30% or more, 40% or more, 50% or more, or even more. In some instances, when the acceptor chromophore is a fluorescent dye, the term efficient energy transfer may refer to a fluorescent quantum yield of 0.05 or more, such as 0.1 or more, 0.2 or more, 0.3 or more, 0.4 or more, 0.5 or more, or even greater. By "amplification" is meant that the signal from the acceptor chromophore is 1.5× or greater when excited by the light harvesting chromophore as compared to direct excitation with incident light of an equivalent intensity, such as 2.0× or greater, 2.5× or greater, 3× or greater, 4× or greater, 5× or greater, 6× or greater, or greater, 8× or greater, 10× or greater, or even greater. The signal may be measured using any convenient method. In some cases, the 1.5× or greater signal refers to an intensity of emitted light. In certain cases, the 1.5× or greater signal refers to an increased signal to noise ratio. In certain embodiments of the polymeric tandem dye, the acceptor chromophore emission is 1.5 fold greater or more when excited by the multichromophore as compared to direct excitation of the acceptor chromophore with incident light.

In some instances, the polymeric tandem dye has an extinction coefficient of $5 \times 10^5$ cm$^{-1}$M$^{-1}$ or more, such as $6 \times 10^5$ cm$^{-1}$M$^{-1}$ or more, $7 \times 10^5$ cm$^{-1}$M$^{-1}$ or more, $8 \times 10^5$ cm$^{-1}$M$^{-1}$ or more, $9 \times 10^5$ cm$^{-1}$M$^{-1}$ or more, such as $1 \times 10^6$ cm$^{-1}$M$^{-1}$ or more, $1.5 \times 10^6$ cm$^{-1}$M$^{-1}$ or more, $2 \times 10^6$ cm$^{-1}$M$^{-1}$ or more, $2.5 \times 10^6$ cm$^{-1}$M$^{-1}$ or more, $3 \times 10^6$ cm$^{-1}$M$^{-1}$ or more, $4 \times 10^6$ cm$^{-1}$M$^{-1}$ or more, $5 \times 10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In some embodiments, the polymeric tandem dye has a molar extinction coefficient of $5\times10^5$ M$^{-1}$ cm$^{-1}$ or more. In certain embodiments, the polymeric tandem dye has a molar extinction coefficient of $1\times10^6$ M$^{-1}$ cm$^{-1}$ or more.

of 20:1 to 3:1, 10:1 to 3:1, 9:1 to 3:1, 5:1 to 3:1 or 4:1 to 3:1, or in the range of 20:1 to 4:1, 20:1 to 5:1, 20:1 to 9:1 or 20:1 to 10:1.

In some instances, the polymeric tandem dye is described by formula (II):

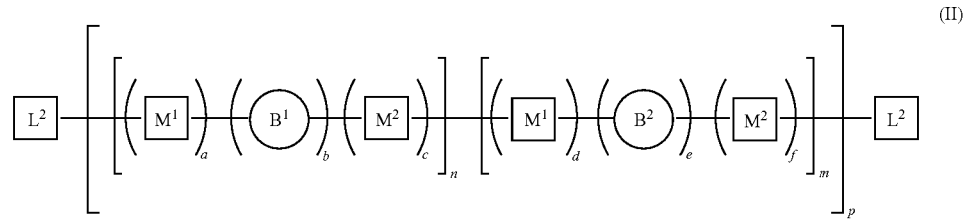

(II)

In certain embodiments, the polymeric tandem dye has a quantum yield of 0.05 or more, such as 0.10 or more, 0.15 or more, 0.20 or more, 0.25 or more, 0.30 or more 0.35 or more, such as 0.40 or more, 0.45 or more, 0.5 or more, or even more. In certain cases, the polymeric tandem dye has a quantum yield of 0.1 or more. In certain instances, the polymeric tandem dye has a quantum yield of 0.3 or more.

Any convenient fluorescent dyes may be utilized in the subject polymeric tandem dyes as an acceptor chromophore. The terms "fluorescent dye" and "fluorophore" are used interchangeably herein. In some embodiments, the acceptor chromophore is a cyanine dye, a xanthene dye, a coumarin dye, a thiazine dye or an acridine dye. Fluorescent dyes of interest include, but are not limited to, fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Lanthanide chelates of interest include, but are not limited to, europium chelates, terbium chelates and samarium chelates. In some embodiments, the polymeric tandem dye includes a polymeric dye linked to an acceptor fluorophore selected from Cy3, Cy3.5, Cy5, Cy5.5, Cy7, Alexa488, Alexa 647 and Alexa700. In certain embodiments, the polymeric tandem dye includes a polymeric dye linked to an acceptor fluorophore selected from Dyomics dyes (such as DY 431, DY 485XL, DY 500XL, DY 530, DY 610, DY 633, DY 640, DY 651, DY 654, DY 682, DY 700, DY 701, DY 704, DY 730, DY 731, DY 732, DY 734, DY 752, DY 754, DY 778, DY 782, DY 800 or DY 831), Biotium CF 555, Cy 3.5, and diethylamino coumarin.

In certain embodiments of the polymeric tandem dye, the ratio of co-monomers which lack an acceptor chromophore to co-monomers which include a linked acceptor chromophore is in the range of 40:1 to 3:1, such as in the range wherein:

$B^1$ and $B^2$ are each independently a BODIPY unit;

each $M^1$ and each $M^2$ are independently a π conjugated co-monomer;

a, b, c, d, e and f are each independently 0, 1 or 2, wherein b+e≥1;

n and m are independently 0 or an integer from 1 to 100,000, wherein n+m≥1;

p is an integer from 1 to 100,000; and each $L^2$ is independently an end group.

In some instances of formula (II), each $L^2$ is independently selected from a terminal group, a π conjugated segment, a linker and a linked specific binding member. In some embodiments of formula (II), when b is 0, a and c are each 1; when e is 0, d and f are each 1; when b is 1, a+c≥1; and when e is 1, d+f≥1. In some embodiments of formula (II), b is 1 and e is 0. In some embodiments of formula (II), b is 0 and e is 1. In some embodiments of formula (II), b is 1 and e is 1. In some embodiments of formula (II), b is 2 and e is 0. In some embodiments of formula (II), b is 0 and e is 2. In some embodiments of formula (II), b is 2. In some embodiments of formula (II), e is 2.

In some instances of formula (II), at least one of $B^1$, $B^2$, $M^1$ and $M^2$ includes -$L^1$-$C^1$, wherein $L^1$ is an optional linker and $C^1$ is the acceptor chromophore. In certain instances of formula (II), at least one of $B^1$ and $B^2$ includes -$L^1$-$C^1$. In some instances of formula (II), at least one of $M^1$ and $M^2$ includes -$L^1$-$C^1$. In some cases of formula (II), $M^1$ includes -$L^1$-$C^1$ and $M^2$ does not. In certain cases of formula (II), $M^2$ includes -$L^1$-$C^1$ and $M^1$ does not. In certain cases of formula (II), $B^1$ includes -$L^1$-$C^1$ and $B^2$ does not. In certain instances of formula (II), $B^2$ includes -$L^1$-$C^1$ and $B^1$ does not.

In some embodiments of formula (II), a is 0. In some instances of formula (II), a is 1. In certain embodiments of formula (II), c is 0. In certain instances of formula (II), c is 1. In some instances of formula (II), a is 1 and c is 0. In certain instances of formula (II), a is 0 and c is 1. In certain cases of formula (II), d is 0. In some instances of formula (II), d is 1. In some embodiments of formula (II), f is 0. In some instances of formula (II), f is 1. In some instances of formula (II), d is 1 and f is 0. In certain instances of formula (II), d is 0 and f is 1.

In some instances, the polymeric tandem dye is described by formula (III):

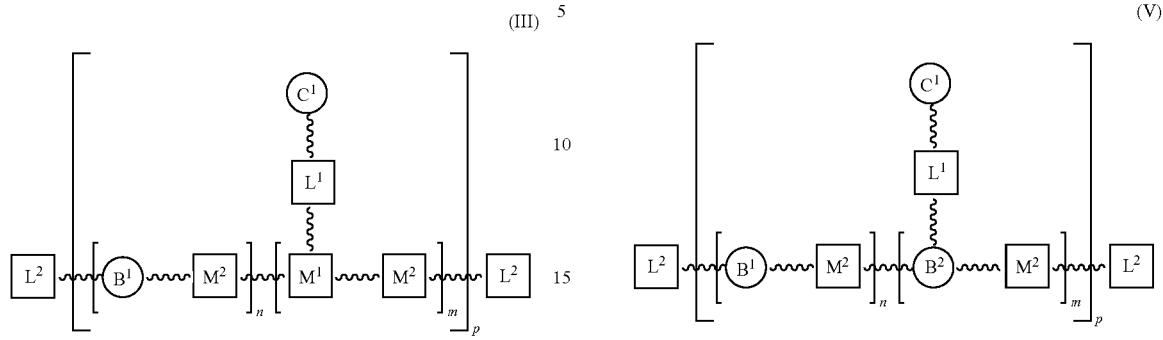

where $B^1$, $B^2$, $M^1$, $M^2$, n, m, p and each $L^2$ is as defined for formula (II), and each $L^1$ is independently an optional linker and each $C^1$ is independently an acceptor chromophore. In some cases of formula (III), each $M^1$ and each $M^2$ are independently a fluorene co-monomer, optionally substituted with a water solubilizing group. In some cases of formula (III), each $M^1$ and each $M^2$ are independently a fused 6-5-6 tricyclic co-monomer, such as a fluorene co-monomer or a carbazole co-monomer, optionally substituted with a water solubilizing group. In certain embodiments of formula (III), the ratio of n to m is in the range of 20:1 to 3:1, such as in the range of 10:1 to 3:1, 9:1 to 3:1, 5:1 to 3:1 or 4:1 to 3:1, or in the range of 20:1 to 4:1, 20:1 to 5:1, 20:1 to 9:1 or 20:1 to 10:1.

In some embodiments, the polymeric tandem dye is described by formula (IV):

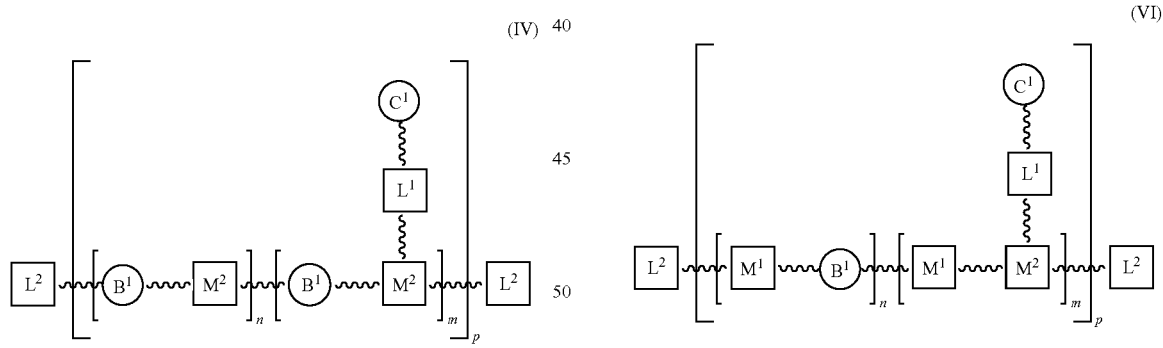

where $B^1$, $M^2$, n, m, p and each $L^2$ is as defined for formula (II), each $L^1$ is an optional linker and each $C^1$ is an acceptor chromophore. In certain embodiments of formula (IV), each $M^2$ is independently a fluorene co-monomer, optionally substituted with a water solubilizing group. In some cases of formula (IV), each $M^2$ is independently a fused 6-5-6 tricyclic co-monomer, such as a fluorene co-monomer or a carbazole co-monomer, optionally substituted with a water solubilizing group. In certain instances of formula (IV), the ratio of n to m is in the range of 20:1 to 3:1, such as in the range of 10:1 to 3:1, 9:1 to 3:1, 5:1 to 3:1 or 4:1 to 3:1, or in the range of 20:1 to 4:1, 20:1 to 5:1, 20:1 to 9:1 or 20:1 to 10:1.

In some embodiments, the polymeric tandem dye is described by formula (V):

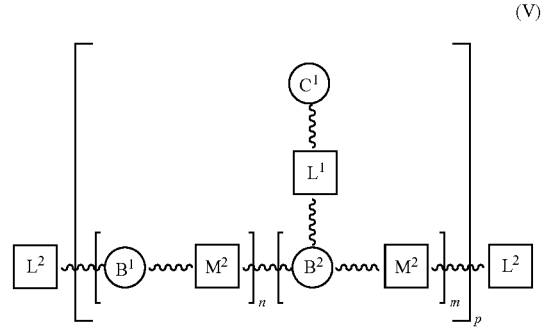

where $B^1$, $B^2$, $M^2$, n, m, p and each $L^2$ is as defined for formula (II), and each $L^2$ is an optional linker and each $C^1$ is an acceptor chromophore. In certain embodiments of formula (V), each $M^2$ is independently a fluorene co-monomer, optionally substituted with a water solubilizing group. In some cases of formula (V), each $M^2$ is independently a fused 6-5-6 tricyclic co-monomer, such as a fluorene co-monomer or a carbazole co-monomer, optionally substituted with a water solubilizing group. In certain instances of formula (V), the ratio of n to m is in the range of 20:1 to 3:1, such as in the range of 10:1 to 3:1, 9:1 to 3:1, 5:1 to 3:1 or 4:1 to 3:1, or in the range of 20:1 to 4:1, 20:1 to 5:1, 20:1 to 9:1 or 20:1 to 10:1.

In some embodiments, the polymeric tandem dye is described by formula (VI):

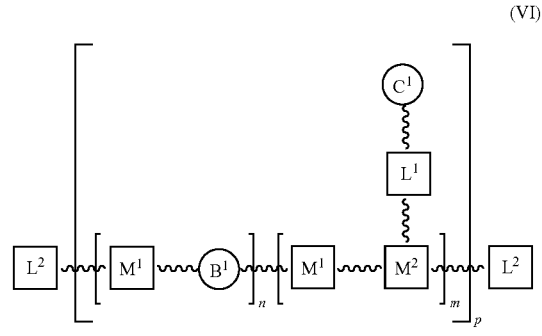

where $B^1$, $M^1$, $M^2$, n, m, p and each $L^2$ is as defined for formula (II) each $L^1$ is an optional linker and each $C^1$ is an acceptor chromophore. In certain embodiments of formula (VI), each $M^1$ is a carbazole co-monomer and each $M^2$ is a fluorene co-monomer, optionally substituted with a water solubilizing group. In some cases of formula (VI), each $M^1$ and each $M^2$ are independently a fused 6-5-6 tricyclic co-monomer, such as a fluorene co-monomer or a carbazole co-monomer, optionally substituted with a water solubilizing group. In certain instances of formula (VI), the ratio of n to m is in the range of 20:1 to 3:1, such as in the range of 10:1 to 3:1, 9:1 to 3:1, 5:1 to 3:1 or 4:1 to 3:1, or in the range of 20:1 to 4:1, 20:1 to 5:1, 20:1 to 9:1 or 20:1 to 10:1.

In some embodiments of formulae (II) to (VI), $B^1$ and $B^2$ are each independently described by the following structure:

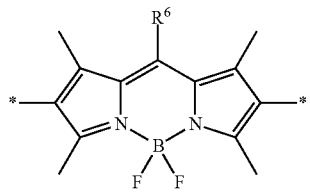

where $R^6$ is an aryl, a heteroaryl or a linker, optionally substituted with one or more water solubilizing groups (WSGs). In certain instances, $R^6$ is a branched linker that links the BODIPY core structure to two or more WSGs. In some cases, $R^6$ is an aryl or heteroaryl moiety that is further substituted with one, two or more WSGs, via optional linkers. In certain embodiments, $R^6$ is a phenyl group substituted with 1, 2, 3 or more hydrophilic polymer substituents (e.g., a PEG or a modified PEG substituent). In certain instances, $R^6$ is a phenyl that is substituted with one, two or three PEG moieties (e.g., —O(CH$_2$CH$_2$O)$_n$R' where R' is H or an alkyl and n is 1-20, e.g., 3-16 such as n is 8-16). In certain instances, $R^6$ is a phenyl that is substituted with one —O(CH$_2$CH$_2$O)$_n$R' group (e.g., at the 2, 3 or 4 position), where R' is H or an alkyl and n is 1-20, e.g., 3-16 such as n is 8-16. In certain instances, $R^6$ is a phenyl that is substituted with two —O(CH$_2$CH$_2$O)$_n$R' groups (e.g., at the 2,4-, 3,4- or 3,5-positions), where each R' is independently H or an alkyl and each n is independently 1-20, e.g., 3-16 such as n is 8-16. In certain instances, $R^6$ is a phenyl that is substituted with three —O(CH$_2$CH$_2$O)$_n$R' groups (e.g., at the 2,4,6-, 2,4,5- or 3,4,5-positions), where each R' is independently H or an alkyl and each n is independently 1-20, e.g., 3-16 such as n is 8-16.

In some instances of formulae (II) to (VI), $B^1$ and $B^2$ are each independently described by the following structure:

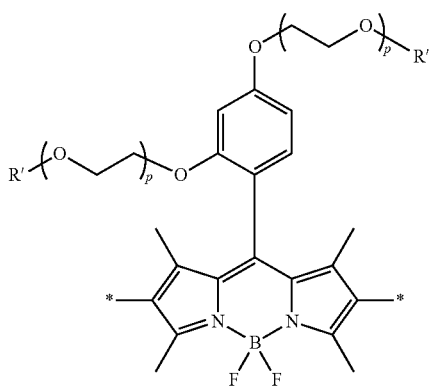

where each R' is independently selected from H and an alkyl; and p is 0 or an integer from 1-20, such as 1, 2, 3, 4, 5, 6, 7, 8, 9, 10, 11 or 12. In certain instances, each R' is methyl. In some cases, each p is 3.

In some embodiments of formulae (II) to (VI), at least one $L^2$ group is -$L^3$-Z where $L^3$ is a linker and Z is a specific binding member (e.g., as described herein). In some embodiments of formulae (II) to (VI), at least one $L^2$ is -$L^3$-Z where $L^3$ is a linker (e.g., as described herein) and Z is a chemoselective tag (e.g., as described herein). In some instances, Z is selected from carboxylic acid, active ester (e.g., N-hydroxy succinimidyl ester (NHS) or sulfo-NHS), amino, maleimide, iodoacetyl and thiol. In certain embodiments of formula (II) to (VI), at least one $L^2$ group is described by the following structure:

*—Ar-L-Z where Ar is a π-conjugated aryl or heteroaryl group, L is a linker and Z is a chemoselective tag or a specific binding member. In certain embodiments of formula (II) to (VI), at least one $L^2$ group is described by one of the following structures:

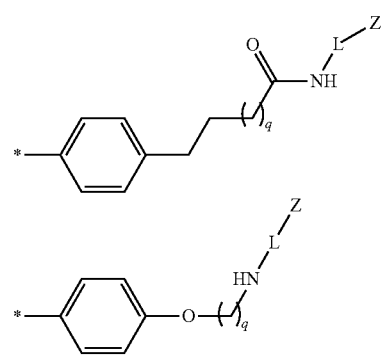

where q is 0 or an integer from 1-12; L is an optional linker; and Z is a chemoselective tag or a specific binding member. In certain embodiments of formula (II) to (VI), at least one $L^2$ group is described by the structure:

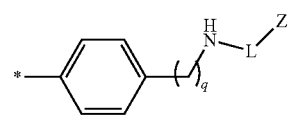

where q is 0 or an integer from 1-12; L is an optional linker; and Z is a chemoselective tag or a specific binding member. In certain instances, —NH-L-Z includes an amide linkage to the chemoselective tag or specific binding member. In certain embodiments, Z is a specific binding member that is a biomolecule. In certain instances, Z is an antibody. In some instances, Z is an antibody fragment or binding derivative thereof. In some cases, the antibody fragment or binding derivative thereof is selected from a Fab fragment, a F(ab')$_2$ fragment, a scFv, a diabody and a triabody.

In some embodiments of formulae (II) to (VI), $C^1$ is selected from a cyanine dye, a xanthene dye, a coumarin dye, a thiazine dye and an acridine dye. In certain cases, the linker is selected from an alkyl, a substituted alkyl, an alkyl-amido, an alkyl-amido-alkyl and a PEG moiety. In certain embodiments of formulae (II) to (VI), the acceptor chromophore $C^1$ is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, Biotium CF 555, Cy 3.5 and diethylamino coumarin. In certain instances of formulae (II) to (VI), the acceptor chromophore is selected from Cy3, Cy3.5, Cy5, Cy5.5, Cy7, Alexa488, Alexa 647 and Alexa700.

In some embodiments, the polymeric tandem dye is described by formula (VII):

(VII)

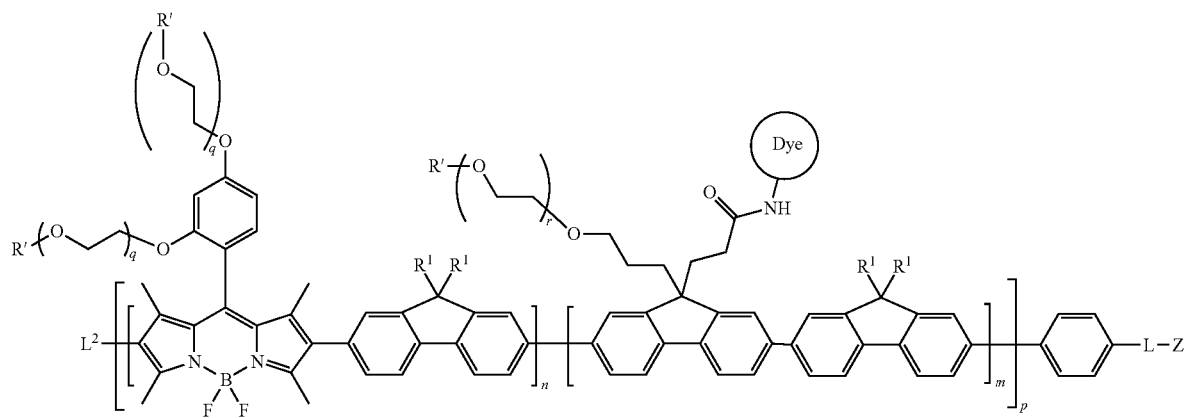

where:

each q and r is independently an integer from 1-20;

each R' is independently hydrogen or an alkyl (e.g., methyl);

each $R^1$ is independently an alkyl, an aryl, a heteroaryl or a linker, optionally substituted with one, two or more water solubilizing groups (WSGs) (e.g., a PEG-disubstituted benzyl or a PEG substituted alkyl);

dye is an acceptor chromophore;

n, m, p and $L^2$ are as defined for formula (II); and

L is a linker and Z is a chemoselective tag or a specific binding member. In certain cases for formula (VII), L is —O—$(CH_2)_n$—NH—, where n is 2-12, such as n is 4. In certain instances, each $R^1$ is described by the structure:

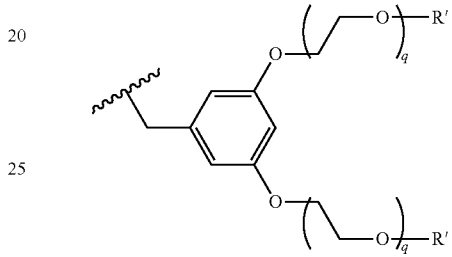

where each q is independently an integer from 2-20, and each R' is independently hydrogen, an alkyl or a substituted alkyl. In certain cases, each R' is methyl. In some cases, each q is 2. In certain cases, each q is 3. In certain cases, each q is 4. In certain cases, each q is 5. In certain cases, each q is 6. In certain cases, each q is 7. In certain cases, each q is 8. In certain cases, each q is 9. In certain cases, each q is 10. In certain cases, each q is 11. In certain instances, $L^2$ is a terminal group.

In some embodiments, the polymeric tandem dye is described by formula (VIII):

(VIII)

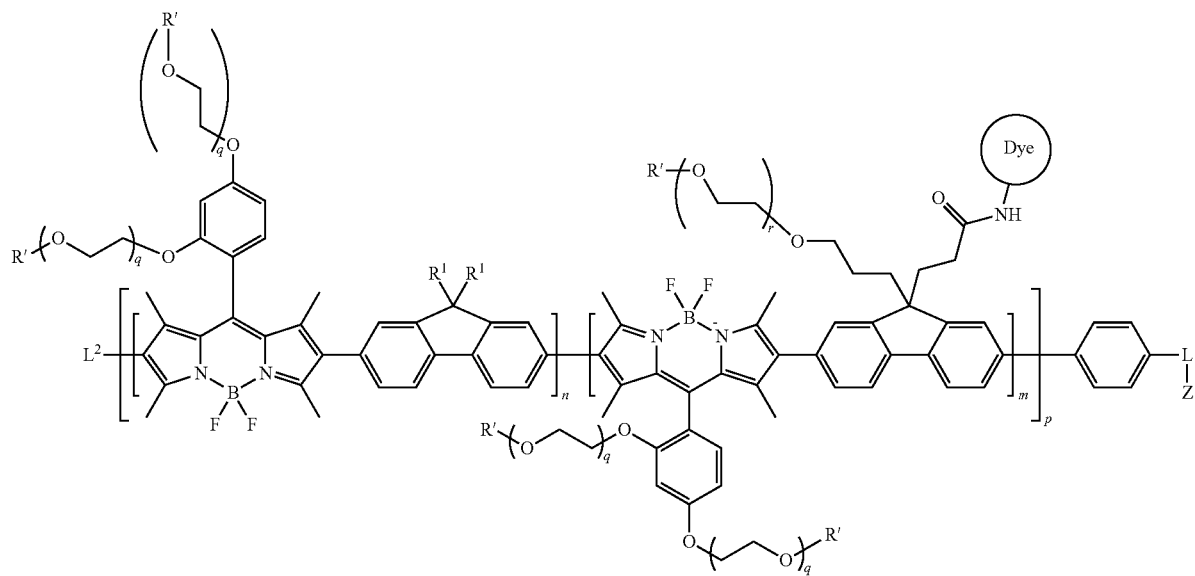

where:
  each q and r is independently an integer from 1-20;
  each R' is independently hydrogen, an alkyl or a substituted alkyl;
  n, m, p and $L^2$ are as defined for formula (II);
  each $R^1$ is independently an alkyl, an aryl, a heteroaryl or a linker, optionally substituted with one, two or more water solubilizing groups (WSGs) (e.g., a PEG-disubstituted benzyl or a PEG substituted alkyl);
  dye is an acceptor chromophore;
  L is a linker and Z is a chemoselective tag or a specific binding member. In certain cases, each R' is methyl. In where each q is independently an integer from 2-20, and each R' is independently hydrogen, an alkyl or a substituted alkyl. In certain cases, each R' is methyl. In some cases, each q is 2. In certain cases, each q is 3. In certain cases, each q is 4. In certain cases, each q is 5. In certain cases, each q is 6. In certain cases, each q is 7. In certain cases, each q is 8. In certain cases, each q is 9. In certain cases, each q is 10. In certain cases, each q is 11. In certain instances, $L^2$ is a terminal group.

In some embodiments, the polymeric tandem dye is described by formula (IX):

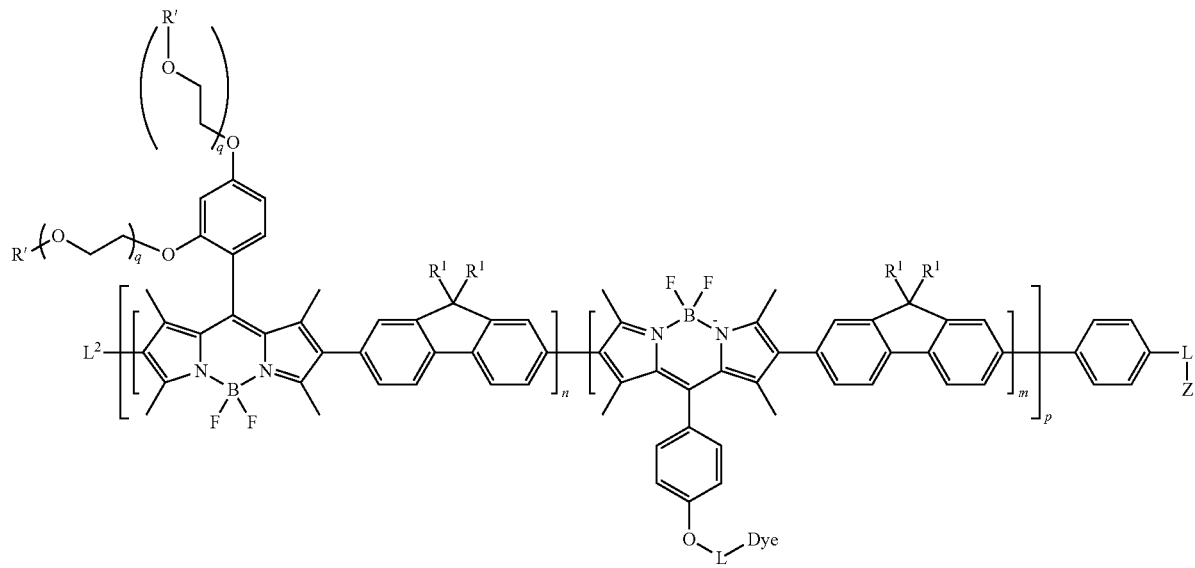

(IX)

certain cases of formula (VIII), L-Z is —O—$(CH_2)_n$—$NH_2$, where n is 2-12 (e.g., n is 2, 3 or 4). In certain cases of formula (VIII), L is —O—$(CH_2)_n$—NH—, where n is 2-12, such as n is 4, and Z is a specific binding member (e.g., a biomolecule). In certain cases of formula (VIII), L-Z is —$(CH_2)_n$—$NH_2$, where n is 2-12 (e.g., n is 2, 3 or 4). In certain cases of formula (VIII), L is —$(CH_2)_n$—NH— and Z is a specific binding member (e.g., a biomolecule), where n is 2-12 (e.g., n is 2, 3 or 4). It is understood that the Dye group of formula (VIII) which is linked to the fluorene co-monomer via a —CONH-Dye linkage may alternatively be linked via with a —NHCO-Dye connection. In such alternate depiction of formula (VIII), L can be —$(CH_2)_n$—CO—, where n is 2-12 (e.g., n is 2, 3 or 4). In certain instances, each $R^1$ is described by the structure:

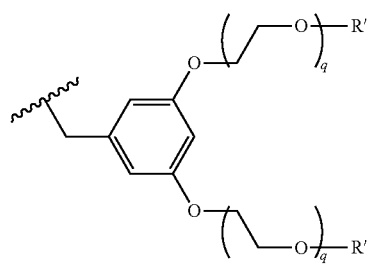

where:
  each q is independently an integer from 1-20;
  each R' is independently hydrogen, an alkyl or a substituted alkyl;
  each $R^1$ is independently an alkyl, an aryl, a heteroaryl or a linker, optionally substituted with one, two or more water solubilizing groups (WSGs) (e.g., a PEG-disubstituted benzyl or a PEG substituted alkyl);
  dye is an acceptor chromophore;
  n, m, p and $L^2$ are as defined in formula (II);
  L is a linker and Z is a chemoselective tag or a specific binding member. In certain cases, each R' is methyl. In certain cases for formula (IX), L is —O—$(CH_2)_n$—NH—, where n is 2-12, such as n is 4. In certain instances, each $R^1$ is described by the structure:

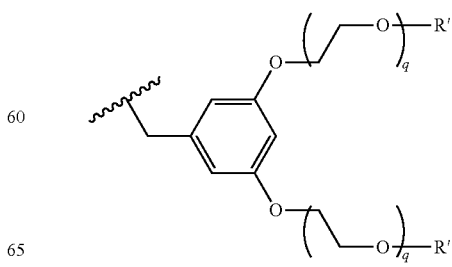

where each q is independently an integer from 2-20, and each R' is independently hydrogen, an alkyl or a substituted alkyl. In certain cases, each R' is methyl. In some cases, each q is 2. In certain cases, each q is 3. In certain cases, each q is 4. In certain cases, each q is 5. In certain cases, each q is 6. In certain cases, each q is 7. In certain cases, each q is 8. In certain cases, each q is 9. In certain cases, each q is 10. In certain cases, each q is 11. In certain instances, $L^2$ is a terminal group.

In some embodiments, the polymeric tandem dye is described by formula (X):

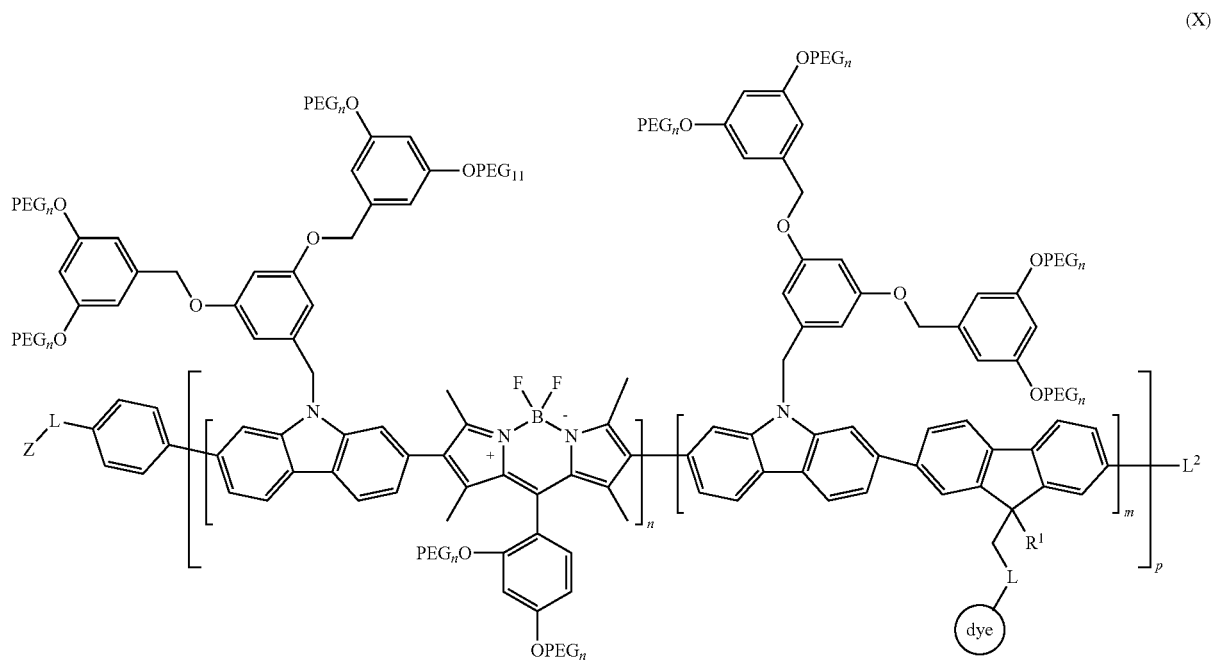

(X)

where:

each PEGn is independently a PEG or a modified PEG of from 1-20 units;

each $R^1$ is independently an alkyl, an aryl, a heteroaryl or a linker, optionally substituted with one, two or more water solubilizing groups (WSGs) (e.g., a PEG-disubstituted benzyl or a PEG substituted alkyl);

dye is an acceptor chromophore;

n, m, p and $L^2$ are as defined in formula (II);

each L is a linker and Z is a chemoselective tag or a specific binding member. In certain cases of formula (X), L is $—O—(CH_2)_n—NH—$, where n is 2-12, such as n is 4. In certain instances of formula (X), $R^1$ is an alkyl. In certain embodiments of formula (X), the ratio of n to m is in the range of 20:1 to 3:1, such as 15:1 to 4:1, 10:1 to 4:1, or 9:1 to 5:1.

In some embodiments, the polymeric tandem dye is described by formula (XI):

(XI)

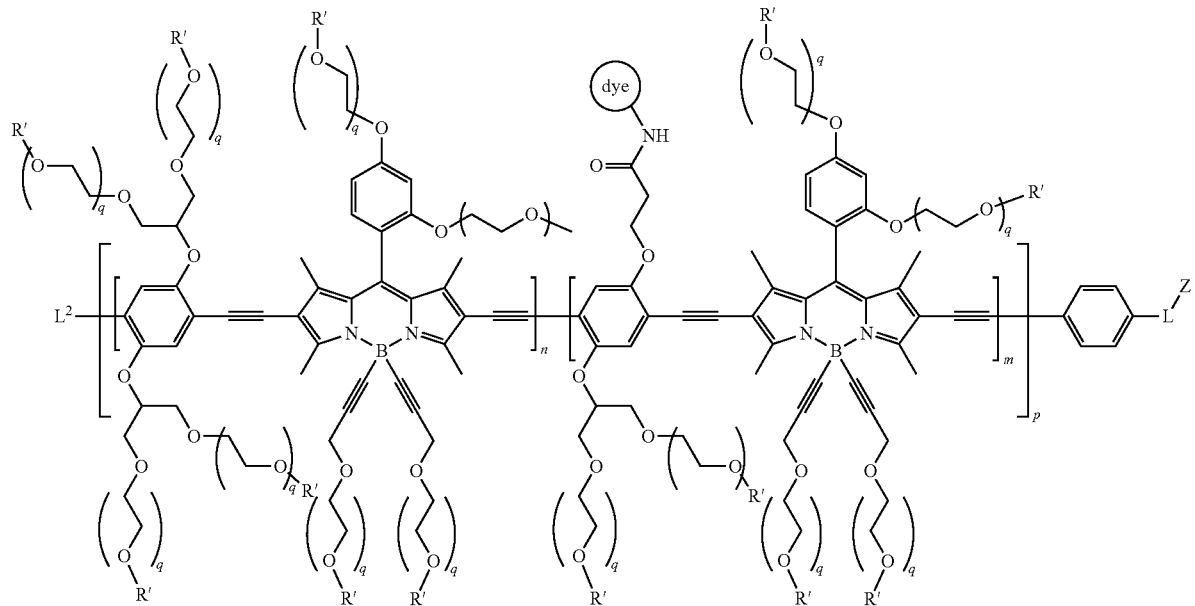

where:
- each q is independently an integer from 1-20;
- each R' is independently hydrogen, an alkyl or a substituted alkyl;
- dye is an acceptor chromophore;
- n, m, p and $L^2$ are as defined in formula (II);

each L is a linker and Z is a chemoselective tag or a specific binding member. In certain cases of formula (XI), L is —O—$(CH_2)_n$—NH—, where n is 2-12, such as n is 4. In certain cases of formula (XI), L is —$(CH_2)_n$—CONH—, where n is 1-12, such as n is 1.

In some embodiments, the polymeric tandem dye is described by formula (XII):

where:
- each q is independently an integer from 1-20;
- each R' is independently hydrogen, an alkyl or a substituted alkyl;
- dye is an acceptor chromophore;
- n, m, p and $L^2$ are as defined in formula (II);

each L is a linker and Z is a chemoselective tag or a specific binding member. In certain cases of formula (XII), L is —O—$(CH_2)_n$—NH—, where n is 2-12, such as n is 4. In certain cases of formula (XII), L is —$(CH_2)_n$—CONH—, where n is 1-12, such as n is 1.

In certain instances of the fluorene co-monomer of any one of formulae (II)-(XII), each $R^1$ or $R^2$ sidechain group is (XII)

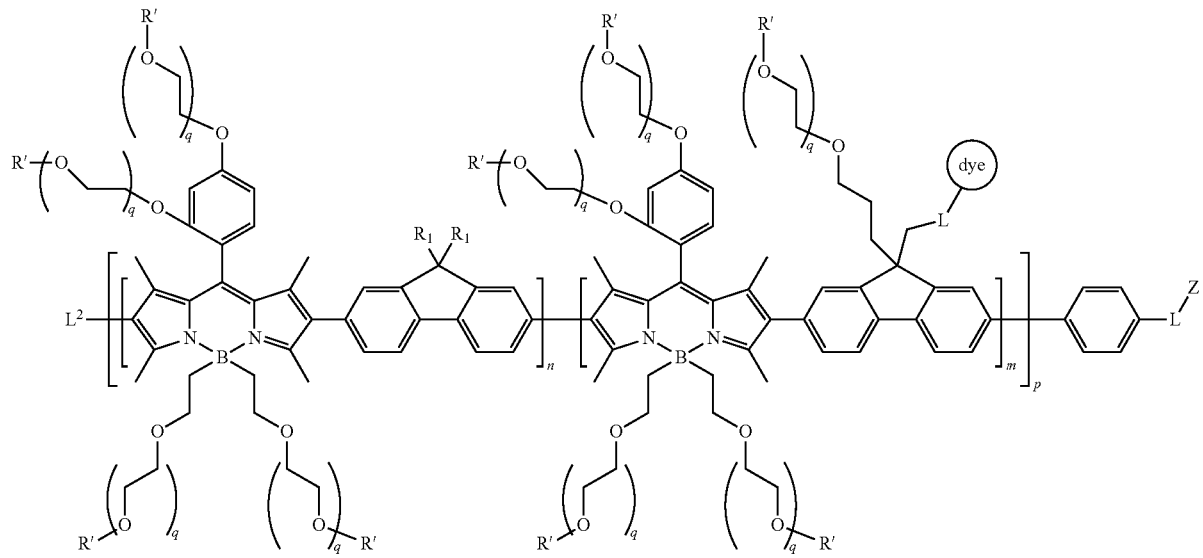

a benzyl group substituted with one, two or three PEG moieties (e.g., —O(CH$_2$CH$_2$O)$_n$R' where R' is H or an alkyl and n is 1-20, e.g., 3-16 such as n is 8-16). In certain instances of the fluorene co-monomer of any one of formulae (II)-(XII), each R$^1$ or R$^2$ sidechain group is a benzyl group substituted with one —O(CH$_2$CH$_2$O)$_n$R' group (e.g., at the 2, 3 or 4 position), where R' is H or an alkyl and n is 1-20, e.g., 3-16 such as n is 8-16. In certain instances of fluorene co-monomer of any one of formulae (II)-(XII), each R$^1$ or R$^2$ sidechain group is a benzyl group substituted with two —O(CH$_2$CH$_2$O)$_n$R' groups (e.g., at the 2,4-, 3,4- or 3,5-positions), where each R' is independently H or an alkyl and each n is independently 1-20, e.g., 3-16 such as n is 8-16. In certain instances of the fluorene co-monomer of any one of formulae (II)-(XII), each R$^1$ or R$^2$ sidechain group is a benzyl group substituted with three —O(CH$_2$CH$_2$O)$_n$R' groups (e.g., at the 2,4,6-, 2,4,5- or 3,4,5-positions), where each R' is independently H or an alkyl and each n is independently 1-20, e.g., 3-16 such as n is 8-16. In certain instances of the fluorene co-monomer of any one of formulae (II)-(XII), each R$^1$ or R$^2$ sidechain group is a lower alkyl group substituted with a trivalent branching group each substituted with two PEG moieties (e.g., a —CO—NR"$_2$ or —O(CH$_2$R")$_2$ trivalent branching group where each R" is independently a PEG moiety (e.g., —O(CH$_2$CH$_2$O)$_n$R' where R' is H or an alkyl and n is 1-20, e.g., 3-16 such as n is 8-16).

It is understood that the polymeric tandem dye of any one of formulae (I) to (XII) can alternatively be represented by a formula which indicates what the mol % values for each co-monomer is in the polymer. For example, in some cases, any one of Formulae (II) to (XII) can be represented by one of the following formula:

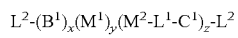

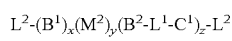

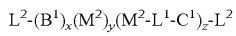

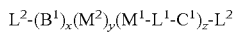

where x, y and z are the mol % values of the co-monomers in the conjugated polymer. In some instances of the formulae, x is 1 mol % or more, such as 2 mol % or more, 3 mol % or more, 4 mol % or more, 5 mol % or more, 10 mol % or more, 15 mol % or more, 20 mol % or more, 25 mol % or more, 30 mol % or more, 35 mol % or more, 40 mol % or more, 45 mol % or more, 50 mol % or more, or even more. In certain instances of the formulae, x ranges from 1 mol % to 50 mol %, such as from 5 mol % to 25 mol % or from 10 mol % to 25 mol %; or such as from 5 mol % to 25 mol % or from 10 mol % to 25 mol %; or such as from 1 mol % to 25 mol %, from 1 mol % to 10 mol %, or from 1 mol % to 5 mol %. In some instances of the formulae, z is 10 mol % or more, such as 15 mol % or more, 20 mol % or more, 25 mol % or more, 30 mol % or more, 35 mol % or more, 40 mol % or more, 45 mol % or more, 50 mol % or more, or even more. In some instances of the formulae, z is 25 mol % or less, such as 20 mol % or less, 15 mol % or less, 10 mol % or less, 8 mol % or less, 6 mol % or less, 5 mol % or less, 2 mol % or less, 1 mol % or less, or even less. In some instances of the formulae, y is 1 mol % or more, such as 5 mol % or more, 10 mol % or more, 15 mol % or more, 20 mol % or more, or 25 mol % or more. In some instances of the formulae, y is 25 mol % or less, such as 20 mol % or less, 15 mol % or less, 10 mol % or less, 8 mol % or less, 6 mol % or less, 5 mol % or less, 2 mol % or less, 1 mol % or less, or even less.

It is understood that for any of the structures and formula depicted herein that in some cases of the subject polymeric tandem dyes the end or terminal groups depicted may be located at the opposite ends to those shown, e.g., the end groups may be switched. In some embodiments of the multichromophores described herein (e.g., formulae (I)-(XII), at least one end group (e.g., L, L$^2$, G$^1$, G$^2$, L-Z) is selected from one of the following structures 1-33:

1

\*—H

2

3

\*—Cl

4

\*—Br

5

\*—SH

6

\*—I

7

\*—B(OH)$_2$

8

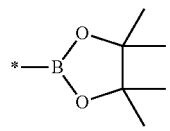

9

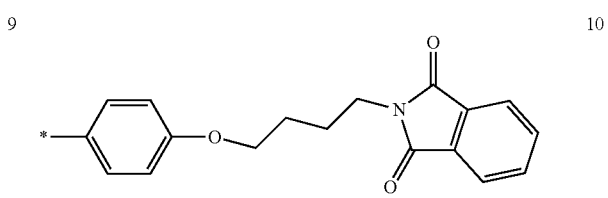

10

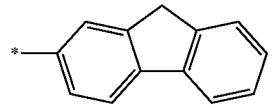

11

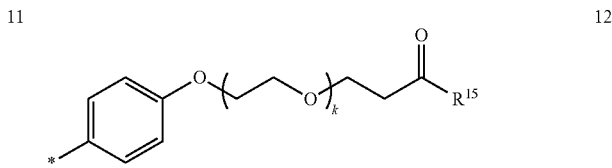

12

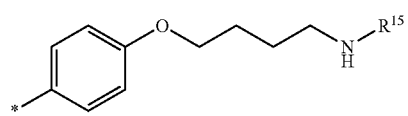

-continued
13
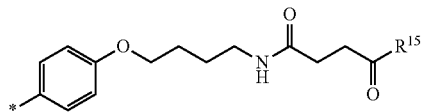
14
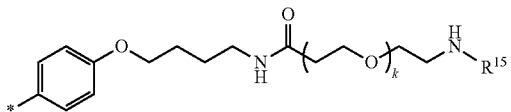
15
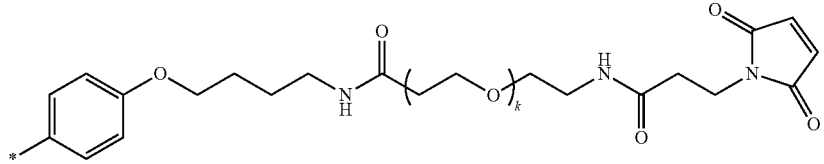
16
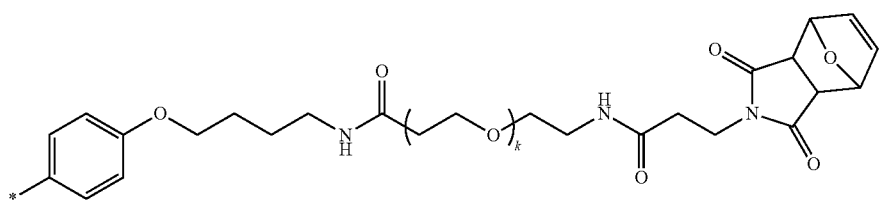
17
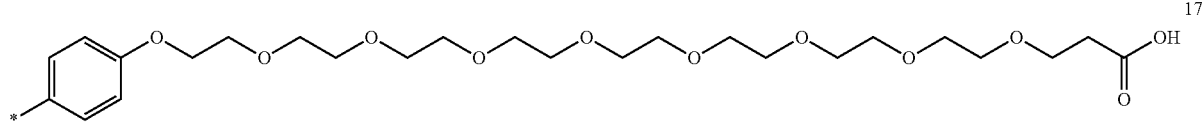
18
19
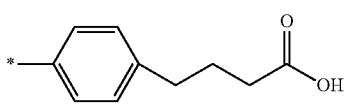
20
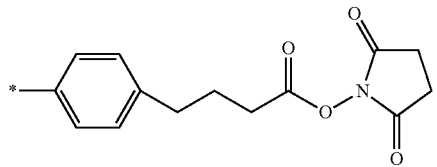
21
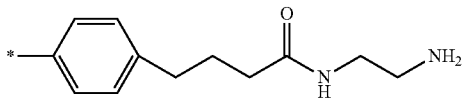
22
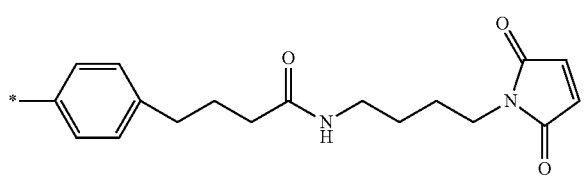
23
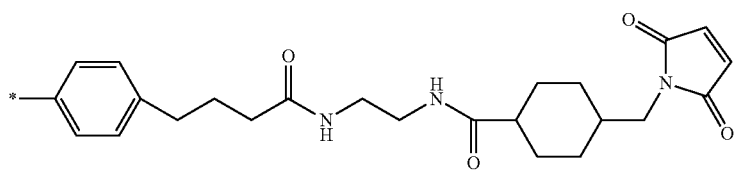
24
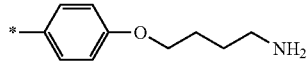
25
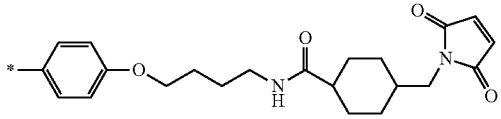
26
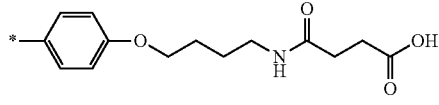
27
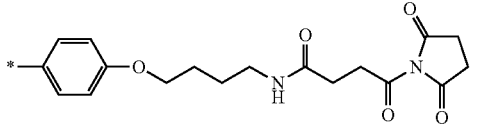

-continued

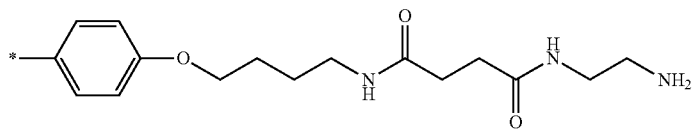
28

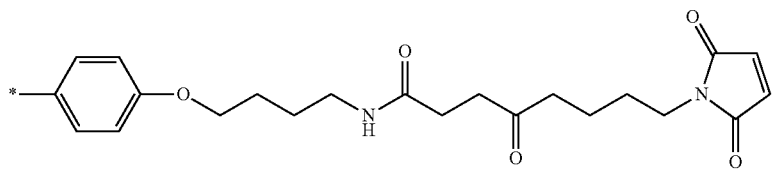
29

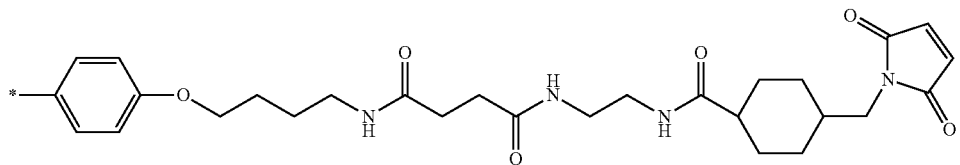
30

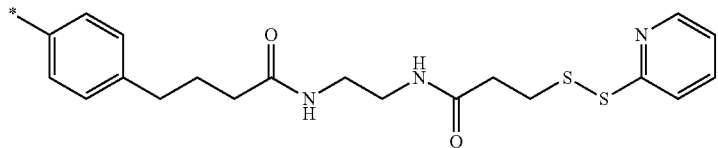
31

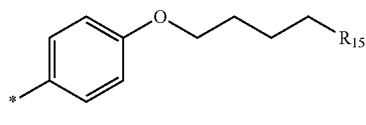
32

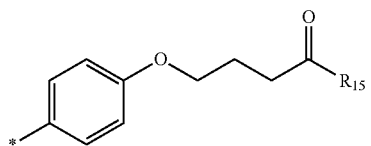
33

*=site for covalent attachment to unsaturated backbone;
wherein R' is independently H, halogen, $C_1$-$C_{12}$ alkyl, ($C_1$-$C_{12}$alkyl)$NH_2$, $C_2$-$C_{12}$ alkene, $C_2$-$C_{12}$ alkyne, $C_3$-$C_{12}$cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$($OCH_2CH_2$)$_{x''}$$OCH_3$ where x'' is independently an integer from 0 to 50, or a benzyl optionally substituted with one or more halogen, hydroxyl, $C_1$-$C_{12}$ alkoxy, or ($OCH_2CH_2$)$_{y''}$$CH_3$ where each y'' is independently an integer from 0 to 50 and R' is different from R; wherein k is 2, 4, 8, 12 or 24; wherein $R^{15}$ is selected from groups l-u having the structure:

*—OH
l

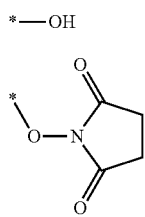
m

-continued

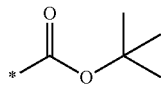
n

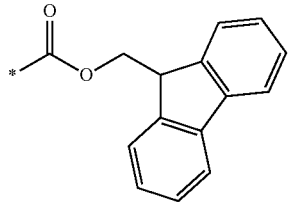
o

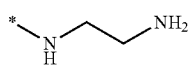
p

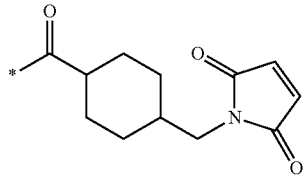
q

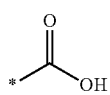
r

-continued

*=site for covalent attachment to backbone.

In some embodiments of the multichromophores described herein (e.g., formulae (I)-(XII)), at least one end group (e.g., L, $L^2$, $G^1$, $G^2$, L-Z) is selected from one of the following structures:

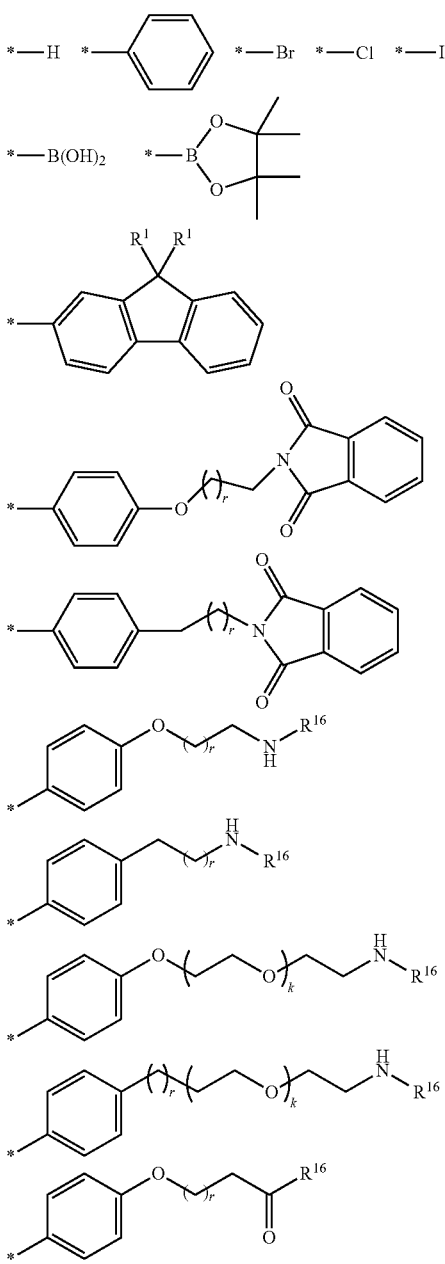

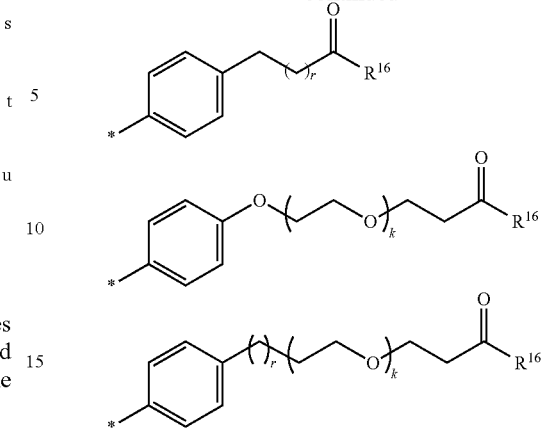

where r is 0 or an integer from 1-50 (e.g., 1-20); k is 0 or an integer from 1-50 (e.g., 1-20); $R^1$ is as defined for any of the fluorene co-monomers described herein; and $R^{16}$ is selected from H, OH, $NH_2$, —$NH(CH_2)_r$-$NH_2$, and —$NH(CH_2)_r$COOH.

Labelled Specific Binding Members

Aspects of the present disclosure include labelled specific binding members. A labelled specific binding member is a conjugate of a subject BODIPY unit-comprising multichromophore (e.g., as described herein) and a specific binding member. The multichromophore may be a polymeric dye. The multichromophore may be polymeric tandem dye. The specific binding member and the multichromophore may be conjugated (e.g., covalently linked) to each other via any convenient locations of the multichromophore, via an optional linker.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

As used herein, the term "proteinaceous" refers to a moiety (e.g., a specific binding member) that is composed of amino acid residues. A proteinaceous moiety may be a polypeptide. In some embodiments, the specific binding member is proteinaceous. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term antibody is meant to include full length antibodies and may refer to a natural antibody from any organism, an engineered antibody, or an antibody generated recombinantly for experimental, therapeutic, or other purposes as further defined below. Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is an antibody. In certain embodiments, the specific binding member is a Fab fragment, a F(ab')$_2$ fragment, a scFv, a diabody or a triabody. In some cases, the specific binding member is a murine antibody or binding fragment thereof. In certain instances, the specific binding member is a recombinant antibody or binding fragment thereof.

In some embodiments, the labelled specific binding member includes: a polymeric tandem dye including: a light harvesting BODIPY unit-comprising multichromophore; an acceptor chromophore covalently linked to the multichromophore in energy-receiving proximity therewith; and a specific binding member covalently linked to the multichromophore. In certain instances of the labelled specific binding member, the light harvesting multichromophore is water soluble. In some instances of the labelled specific binding member, the dye has narrow band spectral features. In some instances of the labelled specific binding member, the dye has low energy absorption bands having a bandwidth of 100 nm or less, such as 50 nm or less. In certain instances of the labelled specific binding member, the multichromophore has a molar extinction coefficient of $5 \times 10^5$ M$^{-1}$ cm$^{-1}$ or more (e.g., as described herein). In certain cases of the labelled specific binding member, the multichromophore has a quantum yield of 0.05 or more (e.g., as described herein). In some embodiments, the labelled specific binding member further includes an acceptor chromophore covalently linked to the multichromophore in energy-receiving proximity therewith, e.g., the multichromophore is a polymeric tandem dye. In some embodiments of the labelled specific binding member, the dye has a ratio of acceptor chromophores to multichromophore repeat units in the range of 1:40 to 1:4, such as a ratio of in the range of 1:20 to 1:4, 1:10 to 1:4, 1:9 to 1:4, 1:8 to 1:4, 1:7 to 1:4, 1:6 to 1:4, or 1:5 to 1:4, or such as a ratio in the range of 1:40 to 1:5, 1:40 to 1:6, 1:40 to 1:7, 1:40 to 1:8, 1:40 to 1:9, 1:40 to 1:10, or 1:40 to 1:20.

In certain cases, the acceptor chromophore is a fluorophore. In some embodiments of the labelled specific binding member, the acceptor chromophore emission is 1.5-fold greater or more (such as 2.0-fold greater or more, 2.5-fold greater or more, 3-fold greater or more, 4-fold greater or more, 5-fold greater or more, 6-fold greater or more, 7-fold greater or more, 8-fold greater or more, 9-fold greater or more, 10-fold greater or more, or even more) when excited by the multichromophore as compared to direct excitation of the acceptor chromophore with incident light.

In some instances of the labelled specific binding member, the multichromophore includes a BODIPY-comprising conjugated segment described by formula (I):

(I)

where B is a BODIPY unit; M is a π conjugated co-monomer; each L is independently selected from a terminal group, a π conjugated segment, a linker and a linked specific binding member; and n is an integer of 1 to 100,000. In certain embodiments of formula (I), the BODIPY unit is described by the structure:

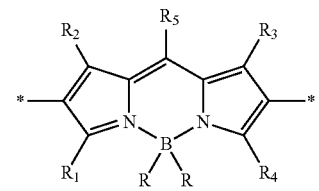

where: $R^1$, $R^2$, $R^3$ and $R^4$ are each independently selected from H, an alkyl and a substituted alkyl; $R^5$ is selected from an alkyl, a substituted alkyl, an aryl, a substituted aryl, a heteroaryl and a substituted heteroaryl, wherein $R^5$ is optionally substituted with a water solubilizing group; and each R is selected from F, OH, H, alkyl, substituted alkyl, aryl, substituted aryl, heteroaryl, substituted heteroaryl, alkoxy, substituted alkoxy, alkynyl and substituted alkynyl. In certain embodiments of formula (I), M is selected from a fluorene co-monomer, a phenylene-vinylene co-monomer, a phenylene-ethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer.

In some embodiments of the labelled specific binding member, the multichromophore is described by the formula (II):

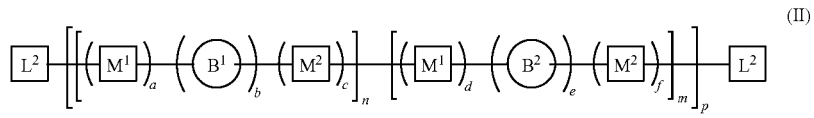

where: $B^1$ and $B^2$ are each independently a BODIPY unit; each $M^1$ and each $M^2$ are independently a π conjugated co-monomer; a, b, c, d, e and f are each independently 0, 1 or 2, wherein b+e≥1; n and m are independently 0 to 100,000, wherein n+m≥1; and one $L^2$ group is a terminal group ($G^1$) and the other $L^2$ group is a linked specific binding member (e.g., L-Z). In certain embodiments of formula (II), at least one of $B^1$, $B^2$, $M^1$ and $M^2$ includes -$L^1$-$C^1$, wherein $L^1$ is an optional linker and $C^1$ is the acceptor chromophore.

In certain embodiments of formula (II), the linked specific binding member is an antibody. In some instances of formula (II), the linked specific binding member is an antibody fragment or binding derivative thereof. In some cases of formula (II), the linked specific binding member is an antibody fragment or binding derivative thereof that is selected from a Fab fragment, a F(ab')$_2$ fragment, a scFv, a diabody and a triabody. In some instances of formula (II), the acceptor chromophore is selected from a cyanine dye, a xanthene dye, a coumarin dye, a thiazine dye and an acridine dye. In certain instances of formula (II), the acceptor chromophore is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, Biotium CF 555, Cy 3.5 and diethylamino coumarin. In some instances of formula (II), the acceptor chromophore is selected from Cy3, Cy3.5, Cy5, Cy5.5, Cy7, Alexa488, Alexa 647 and Alexa700.

In some embodiments, the labelled specific binding member is a polymeric tandem dye of formula (III), where one $L^2$ group is a linked specific binding member. In some embodiments, the labelled specific binding member is a polymeric tandem dye of formula (IV), where one $L^2$ group is a linked specific binding member. In some embodiments, the labelled specific binding member is a polymeric tandem dye of formula (V), where one $L^2$ group is a linked specific binding member. In some embodiments, the labelled specific binding member is a polymeric tandem dye of formula (VI), where one $L^2$ group is a linked specific binding member.

In some embodiments, the labelled specific binding member is a polymeric tandem dye of formula (VII), where Z is a specific binding member. In some embodiments, the labelled specific binding member is a polymeric tandem dye of formula (VIII), where Z is a specific binding member. In some embodiments, the labelled specific binding member is a polymeric tandem dye of formula (IX), where Z is a specific binding member. In some embodiments, the labelled specific binding member is a polymeric tandem dye of formula (X), where Z is a specific binding member. In some embodiments, the labelled specific binding member is a polymeric tandem dye of formula (XI), where Z is a specific binding member. In some embodiments, the labelled specific binding member is a polymeric tandem dye of formula (XII), where Z is a specific binding member.

In certain embodiments, the labelled specific binding member is described by the following structure:

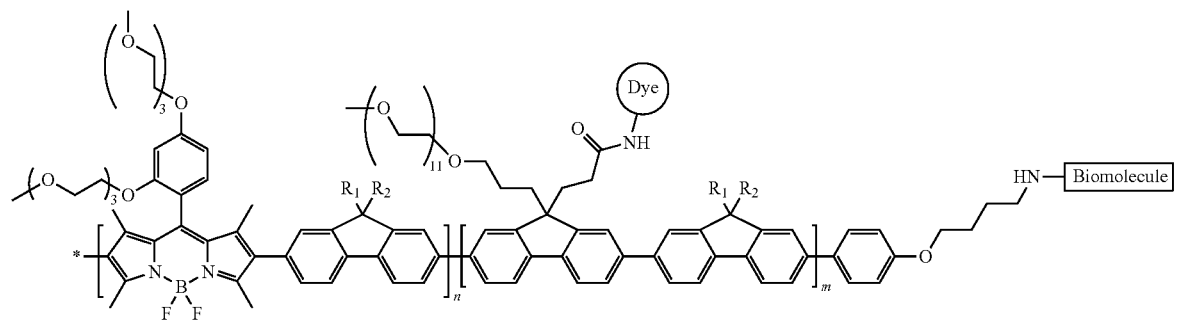

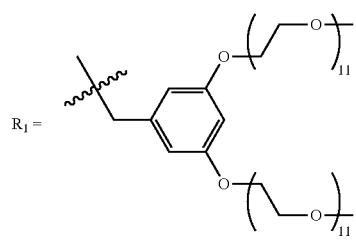

In certain embodiments, the labelled specific binding member is described by the following structure:
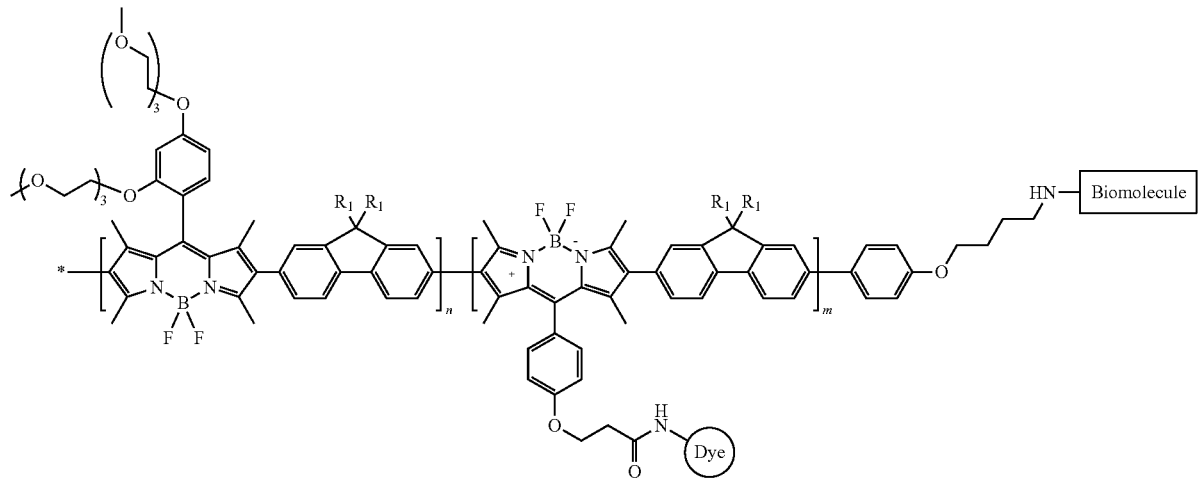
In certain embodiments, the labelled specific binding member is described by the following structure:
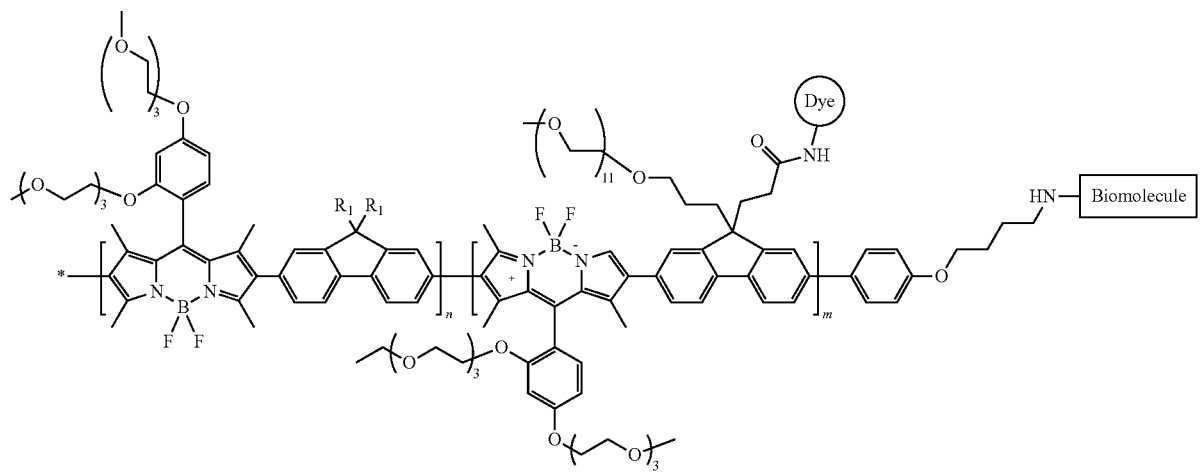

In certain embodiments, the labelled specific binding member is described by the following structure:
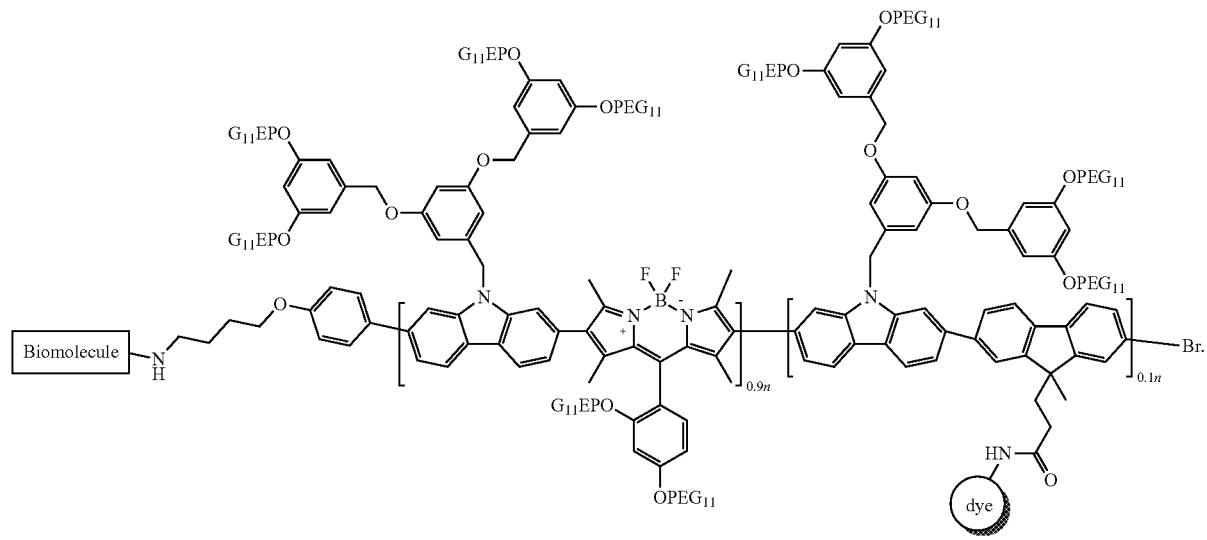
In certain embodiments, the labelled specific binding member is described by the following structure:
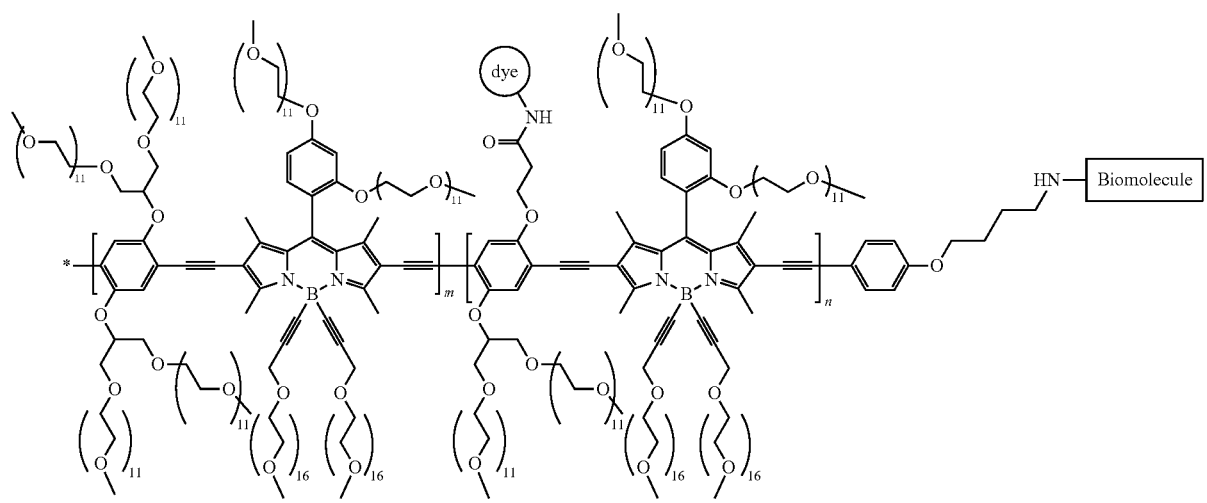

In certain embodiments, the labelled specific binding member is described by the following structure:

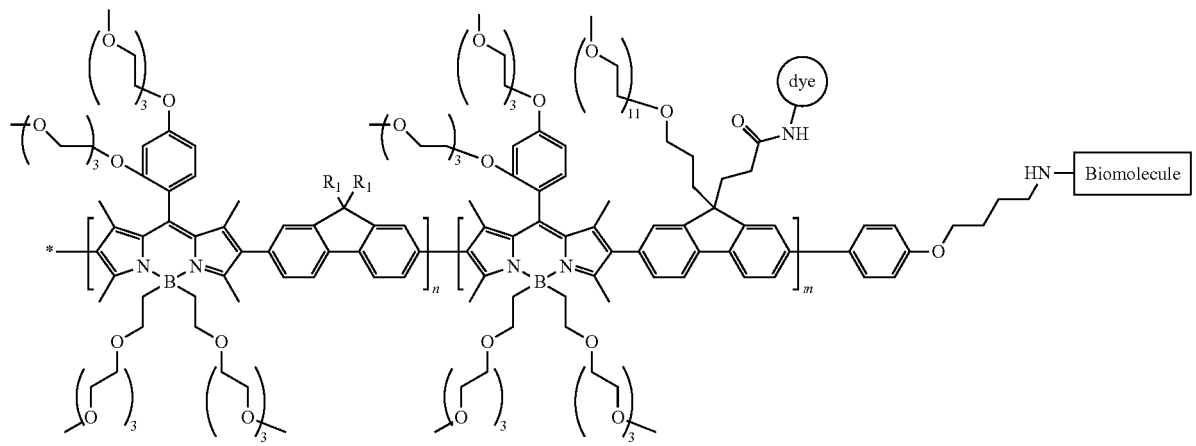

Also provided are polymeric tandem dye precursors of any one of the structures shown above which include a terminal amino functional group suitable for conjugation to the "Biomolecule". The structures of such polymeric tandem dye precursors may be represented by replacing the "Biomolecule" group depicted in the structures above with an "H". In some instances of the structures depicted above, the linked "dye" is a linked fluorescent dye.

Methods

As summarized above, aspects of the invention include methods of evaluating a sample for the presence of a target analyte. In some embodiments, the method includes: (a) contacting the sample with a polymeric dye conjugate that specifically binds the target analyte to produce a labelling composition contacted sample; and (b) assaying the labelling composition contacted sample for the presence of a polymeric dye conjugate-target analyte binding complex to evaluate whether the target analyte is present in the sample. In certain embodiments of the method, the polymeric dye conjugate includes: (i) a light harvesting BODIPY unit-comprising multichromophore (e.g., as described herein); (ii) an acceptor chromophore covalently linked to the multichromophore in energy-receiving proximity therewith; and (iii) a specific binding member (e.g., as described herein).

Any convenient method may be used to contact the sample with a polymeric dye conjugate that specifically binds to the target analyte to produce the labelling composition contacted sample. As used herein, the terms "polymeric dye conjugate" and "labelled specific binding member" are used interchangeably. In some instances, the sample is contacted with the polymeric dye conjugate under conditions in which the specific binding member specifically binds to the target analyte, if present. For specific binding of the specific binding member of the conjugate with the target analyte, an appropriate solution may be used that maintains the biological activity of the components of the sample and the specific binding member. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the solution may be selected depending on the components of the sample which are included.

The temperature at which specific binding of the specific binding member of the conjugate to the target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the target analyte. In certain instances, the temperature is 25° C., 30° C., 35° C. or 37° C. In certain cases, the specific binding member is an antibody or fragment thereof and the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the polymeric dye conjugate. Specific binding members of interest include, but are not limited to, those agents that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins or cell markers may be targeted for specific binding to polymeric dye conjugates in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods.

In some embodiments, the target analyte is associated with a cell. In certain instances, the target analyte is a cell surface marker of the cell. In certain cases, the cell surface marker is selected from a cell receptor and a cell surface antigen. In some instances, the target analyte is an intracellular target, and the method further includes lysing the cell. In certain instances, the method further includes extracting proteins from the cell. Any convenient methods and agents may be utilized in lysing the cell. Methods and agents of interest include those cell lysing and protein extraction methods and agents described at www.piercenet.com/method/traditional-methods-cell-lysis.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The subject labelled specific binding members find use in the subject methods, e.g., for labeling a target cell, particle, target or analyte with a polymeric dye or polymeric tandem dye. For example, labelled specific binding members find use in labeling cells to be processed (e.g., detected, analyzed, and/or sorted) in a flow cytometer. The labelled specific binding members may include antibodies that specifically bind to, e.g., cell surface proteins of a variety of cell types (e.g., as described herein). The labelled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. labelled specific binding members may be used in any application that includes (or may include) antibody-mediated labeling of a cell, particle or analyte.

In some embodiments, the polymeric dye conjugate includes a polymeric tandem dye (e.g., as described herein). As such, in some embodiments, the polymeric dye conjugate further includes an acceptor chromophore covalently linked to the multichromophore in energy-receiving proximity therewith. In certain embodiments, the conjugate is described by formula (II):

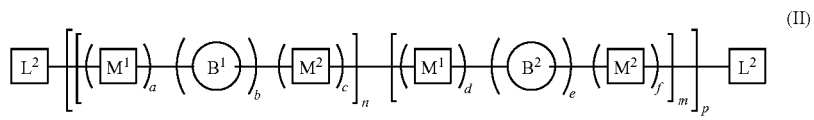

(II)

where $B^1$ and $B^2$ are each independently a BODIPY unit; each $M^1$ and each $M^2$ are independently a π conjugated co-monomer; a, b, c, d, e and f are each independently 0, 1 or 2, wherein b+e≥1; n and m are independently 0 to 100,000, wherein n+m≥1; and one $L^2$ group is a terminal group ($G^1$) and the other $L^2$ group is a linked specific binding member. In certain embodiments, at least one of $B^1$, $B^2$, $M^1$ and $M^2$ includes -$L^1$-$C^1$, wherein $L^1$ is an optional linker and $C^1$ is the acceptor chromophore.

Once the sample has been contacted with the polymeric dye conjugate, any convenient methods may be utilized in assaying the labelling composition contacted sample that is produced for the presence of a polymeric dye conjugate-target analyte binding complex. The polymeric dye conjugate-target analyte binding complex is the binding complex that is produced upon specific binding of the specific binding member of the conjugate to the target analyte, if present. Assaying the labelling composition contacted sample may include detecting a fluorescent signal from the binding complex, if present. In some cases, the assaying includes a separating step where the target analyte, if present, is separated from the sample. A variety of methods may be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds the target analyte. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the polymeric dye conjugate produce a sandwich complex that may be isolated and detected, if present, using any convenient methods. In some embodiments, the method further includes flow cytometrically analyzing the polymeric dye conjugate-target analyte binding complex, i.e., a fluorescently labelled target analyte. Assaying for the presence of a polymeric dye conjugate-target analyte binding complex may provide assay results (e.g., qualitative or quantitative assay data) which can be used to evaluate whether the target analyte is present in the sample.

Any convenient supports may be utilized in the subject methods. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method further includes detecting the labelled target. Detecting the labelled target may include exciting the multichromophore with one or more lasers and subsequently detecting fluorescence emission from the polymeric dye using one or more optical detectors.

Also provided are methods of labelled a target molecule. The subject polymeric dyes, including tandem dyes, find use in a variety of methods of labelling, separation, detection and/or analysis. In some embodiments, the method includes: contacting the target molecule with a polymeric tandem dye to produce a labelled target molecule, wherein the polymeric tandem dye includes: a light harvesting BODIPY unit-comprising multichromophore (e.g., as described herein); and a conjugation tag. In certain instances, the polymeric dye is itself fluorescent. In some embodiments, the polymeric dye is a polymeric tandem dye. As such, in some cases, the polymeric dye further includes an acceptor chromophore covalently linked to the multichromophore in energy-receiving proximity therewith. As used herein, the term "labelled target molecule" refers to a target molecule that is covalently linked to a subject multichromophore.

In some embodiments, the polymeric dye is described by formula (II):

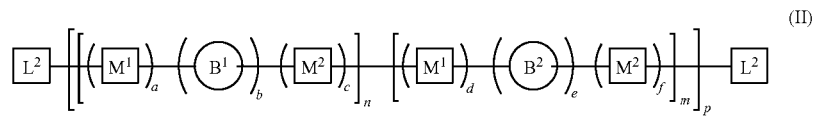

where: $B^1$ and $B^2$ are each independently a BODIPY unit; each $M^1$ and each $M^2$ are independently a π conjugated co-monomer; a, b, c, d, e and f are each independently 0, 1 or 2, wherein b+e≥1; n and m are independently 0 to 100,000, wherein n+m≥1; and one $L^2$ group is a terminal group ($G^1$) and the other $L^2$ group is the conjugation tag. In certain instances of formula (II), at least one of $B^1$, $B^2$, $M^1$ and $M^2$ includes -$L^1$-$C^1$, wherein $L^1$ is an optional linker and $C^1$ is the acceptor chromophore.

As used herein the term "conjugation tag" refers to a group that includes a chemoselective functional group (e.g., as described herein) that can covalently link with a compatible functional group of a target molecule, after optional activation and/or deprotection. Any convenient conjugation tags may be utilized in the subject polymeric dyes in order to conjugate the dye to a target molecule of interest. In some embodiments, the conjugation tag includes a terminal functional group selected from an amino, a carboxylic acid or a derivative thereof, a thiol, a hydroxyl, a hydrazine, a hydrazide, a azide, an alkyne and a protein reactive group (e.g. amino-reactive, thiol-reactive, hydroxyl-reactive, imidazolyl-reactive or guanidinyl-reactive).

Any convenient methods and reagents may be adapted for use in the subject labelling methods in order to covalently link the conjugation tag to the target molecule. Methods of interest for labelling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa.

Any convenient target molecules may be selected for labelling utilizing the subject methods. Target molecules of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the target molecule is a specific binding member (e.g., as described herein). In certain instances, the specific binding member is an antibody. In some instances, the specific binding member is an antibody fragment or binding derivative thereof. In some case, the antibody fragment or binding derivative thereof is selected from a Fab fragment, a F(ab')$_2$ fragment, a scFv, a diabody and a triabody.

In some cases, the method includes a separating step where the labelled target molecule is separated from the reaction mixture, e.g., excess reagents or unlabeled target. A variety of methods may be utilized to separate a target from a sample, e.g., via immobilization on a support, precipitation, chromatography, and the like.

In some instances, the method further includes detecting and/or analyzing the labelled target molecule. In some instances, the method further includes fluorescently detecting the labelled target molecule. Any convenient methods may be utilized to detect and/or analyse the labelled target molecule in conjunction with the subject methods and compositions. Methods of analyzing a target of interest that find use in the subject methods, include but are not limited to, flow cytometry, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, nucleic acid sequencing, fluorescence in-situ hybridization (FISH), protein mass spectroscopy, flow cytometry, and the like.

Detection may be achieved directly via a reporter molecule, or indirectly by a secondary detection system. The latter may be based on any one or a combination of several different principles including but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). The label used for direct or indirect detection may be any detectable reported molecule. Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. Labels of interest include, but are not limited to fluorophores, luminescent labels, metal complexes, radioisotopes, biotin, streptavidin, enzymes, or other detection labels and combination of labels such as enzymes and a luminogenic substrate. Enzymes of interest and their substrates include alkaline phosphatase, horseradish peroxidase, beta-galactosidase, and luciferase, and the like. More than one antibody of specific and/or non-specific nature might be labelled and used simultaneously or sequentially to enhance target detection, identification, and/or analysis. Labels of interest include, but are not limited to FITC (fluorescein isothiocyanate) AMCA (7-amino-4-methylcoumarin-3-acetic acid), Alexa Fluor 488, Alexa Fluor 594, Alexa Fluor 350, DyLight350, phycoerythrin, allophycocyanin and stains for detecting nuclei such as Hoechst 33342, LDS751, TO-PRO and DAPI.

Systems

Aspects of the invention further include systems for use in practicing the subject methods and compositions. A sample analysis system may include a flow channel loaded with a sample and a labelled specific binding member. In some embodiments, the system is a flow cytometric system including: a flow cytometer including a flow path; a composition in the flow path, wherein the composition includes: a sample; and a labelled specific binding member (e.g., as described herein). In some instances of the system, the labelled specific binding member includes a light harvesting BODIPY unit-comprising multichromophore; and a specific binding member that specifically binds a target analyte and is covalently linked to the multichromophore. The multichromophore may be a polymeric dye that is itself fluorescent. The multichromophore may be a polymeric tandem dye. In certain instances, the labelled specific binding member further includes an acceptor chromophore covalently linked to the multichromophore in energy-receiving proximity therewith. In some embodiments, the labelled specific binding member is described by formula (II):

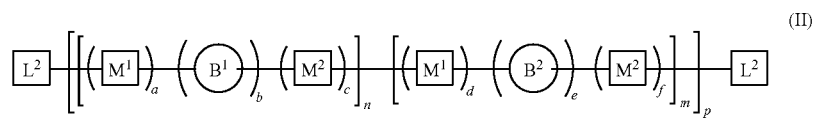

(II)

where: $B^1$ and $B^2$ are each independently a BODIPY unit; each $M^1$ and each $M^2$ are independently a π conjugated co-monomer; a, b, c, d, e and f are each independently 0, 1 or 2, wherein b+e≥1; n and m are independently 0 to 100,000, wherein n+m≥1; and one $L^2$ group is a terminal group ($G^1$) and the other $L^2$ group is the conjugation tag. In certain instances of formula (II), at least one of $B^1$, $B^2$, $M^1$ and $M^2$ includes -$L^1$-$C^1$, wherein $L^1$ is an optional linker and $C^1$ is the acceptor chromophore.

In certain embodiments of the system, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from a cell receptor and a cell surface antigen.

In certain aspects, the system may also include a light source configured to direct light to an assay region of the flow channel. The system may include a detector configured to receive a signal from an assay region of the flow channel, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Flow cytometers of interest include, but are not limited, to those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel. The fluorimeter or microscope may also include a detector configured to receive a signal from an assay region of the flow channel, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above.

A kit may include a light harvesting BODIPY unit-comprising multichromophore (e.g., as described herein); and one or more components selected from a polymeric tandem dye, a fluorophore, a specific binding member, a specific binding member conjugate, a support bound specific binding member, a cell, a support, a biocompatible aqueous elution buffer, and instructions for use. In some embodiments of the kit, the multichromophore is covalently linked to a specific binding member. In some instances, the specific binding member is an antibody. In certain instances, the specific binding member is an antibody fragment or binding derivative thereof. In certain cases, the antibody fragment or binding derivative thereof is selected from a Fab fragment, a F(ab')2 fragment, a scFv, a diabody and a triabody. The multichromophore may be a polymeric dye that is itself fluorescent. The multichromophore may be a polymeric tandem dye. In some cases, the multichromophore further includes an acceptor chromophore covalently linked to the multichromophore in energy-receiving proximity therewith.

In certain embodiments, the kit finds use in evaluating a sample for the presence of a target analyte, such as an intracellular target. As such, in some instances, the kit includes one or more components suitable for lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the multichromophore, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The compositions, methods and systems as described herein may find use in a variety of applications, including diagnostic and research applications, in which the labelling detection and/or analysis of a target of interest is desirable. Such applications include methodologies such as cytometry, microscopy, immunoassays (e.g. competitive or non-competitive), assessment of a free analyte, assessment of receptor bound ligand, and so forth. The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions and methods find use in applications where the evaluation of a sample for the presence of a target analyte is of interest.

In some cases, the methods and compositions find use in any assay format where the detection and/or analysis of a target from a sample is of interest, including but not limited to, flow cytometry, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

The following examples are offered by way of illustration and not by way of limitation.

EXPERIMENTAL

Example 1

A series of tandem dyes were prepared based on a core Structure 1 depicted below including a series of linked fluorophores, DY 633, DY 651, DY 682 and DY 752.

Structure 1

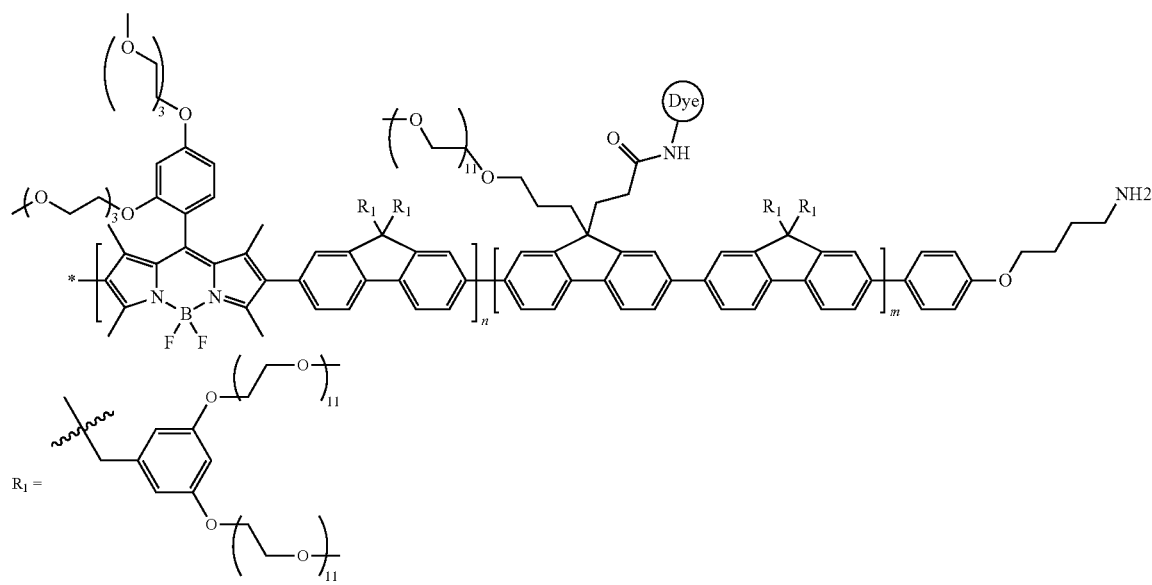

FIG. 1 shows absorption and emission of polymeric tandem dyes based on core Structure 1 attached to a variety of acceptor dyes at the internal linker site (e.g., dyes DY 633, DY 651, DY682 and DY 752). No specific binding member is attached to these structures.

Figure 2:
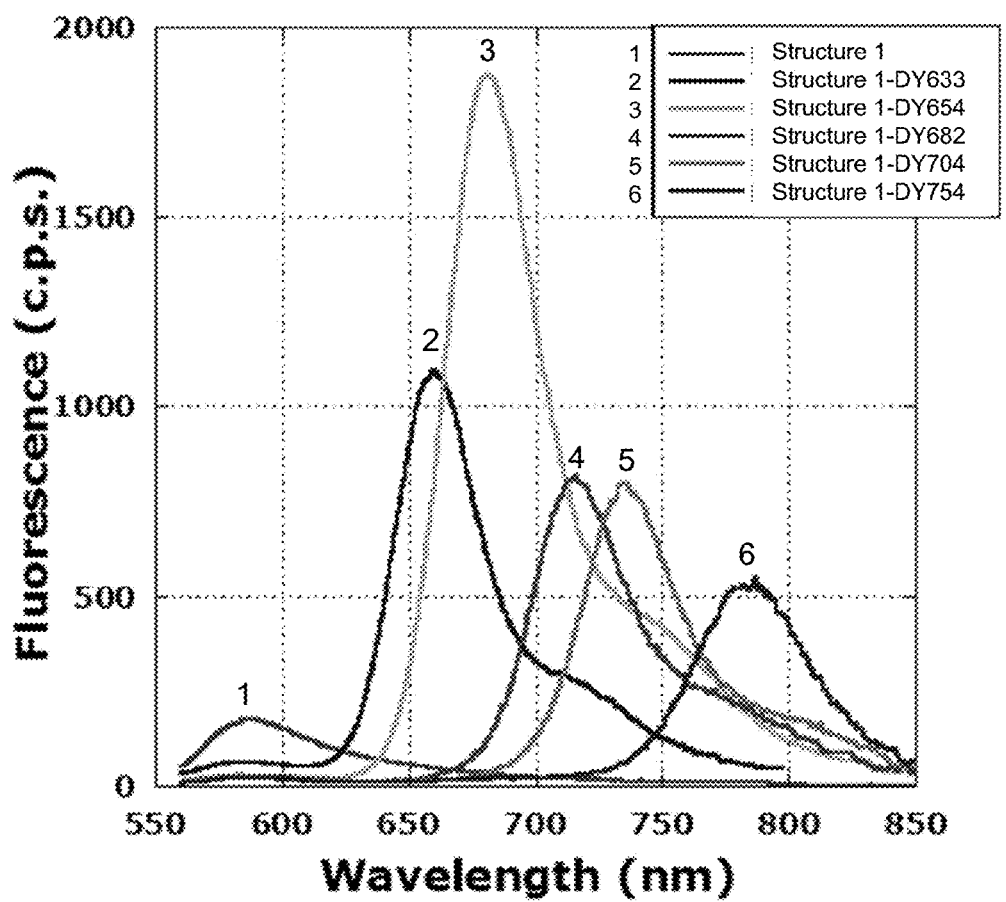
FIG. 2 illustrates absorption and emission of exemplary polymeric tandem dyes with a variety of dye molecules attached at the internal linker site. Absorption for all solutions is 0.04 OD. Note that the emission intensity is significantly higher for polymers with an acceptor chromophore attached relative to the polymer alone. No specific binding member is attached to these polymers.

A second series of tandem dyes were prepared based on a core Structure 1 depicted above including a series of linked of acceptor dye fluorophores at the internal linker site, DY 633, DY 654, DY682, DY 754 and DY 752. FIG. 2 illustrates fluorescence of these polymeric tandem dyes based on Structure 1 with a variety of dye molecules attached at the internal linker site. Absorption for all solutions is 0.04 OD. Note that the emission intensity is significantly higher for polymers with an acceptor chromophore attached relative to the polymer alone. No specific binding member is attached to these polymers.

The quantum yield of the tandem pairs is brighter than the core polymer alone. For structure 1 a range of acceptor chromophores were attached and the resulting tandem pairs were compared spectroscopically to the polymer without a secondary chromophore. All solutions prepared were at the same optical density for the excitation wavelength of 562 nm. As can be seen in FIG. 2, the peak height and peak area for the tandem pairs (peaks 2-6) are all larger than the emission from the underlying polymer (peak 1). In this way extensive prototyping of increasingly bright underlying polymers is unnecessary and the tandem pairs are limited in brightness largely due to the quantum yield of the acceptor.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A water soluble polymeric tandem dye comprising:
a light harvesting multichromophore that is a conjugated polymer comprising π conjugated BODIPY units; and
an acceptor chromophore covalently linked to the multichromophore in energy-receiving proximity therewith.

2. The dye according to claim 1, wherein the multichromophore comprises a BODIPY-comprising conjugated segment described by formula (I):

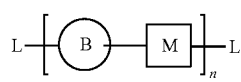

(I)

wherein:
B is a BODIPY unit;
M is a π conjugated co-monomer;

each L is independently selected from the group consisting of a terminal group, a π conjugated segment, a linker and a linked specific binding member; and
n is an integer of 2 to 100,000.

3. The dye according to claim 2, wherein the BODIPY unit is described by the structure:

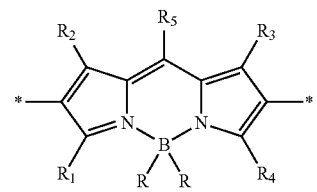

wherein:
$R^1$, $R^2$, $R^3$ and $R^4$ are each independently selected from H, an alkyl and a substituted alkyl;
$R^5$ is selected from the group consisting of an alkyl, a substituted alkyl, an aryl, a substituted aryl, a heteroaryl, a substituted heteroaryl, wherein $R^5$ is optionally substituted with a water solubilizing group; and
each R is selected from the group consisting of F, OH, H, alkyl, substituted alkyl, aryl, substituted aryl, heteroaryl, substituted heteroaryl, alkoxy, substituted alkoxy, alkynyl and substituted alkynyl.

4. The dye according to claim 1, wherein the multichromophore is described by the formula (II):

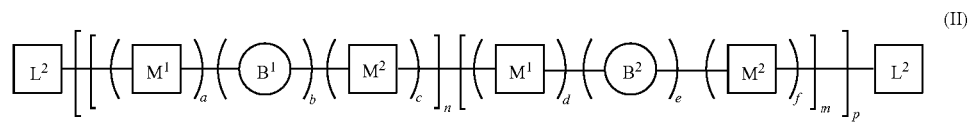

(II)

wherein:
$B^1$ and $B^2$ are each independently a BODIPY unit;
each $M^1$ and each $M^2$ are independently a π conjugated co-monomer;
a, b, c, d, e and f are each independently 0, 1 or 2, wherein b+e≥1;
n and m are independently 0 or an integer from 1 to 100,000, wherein n+m≥1;
p is an integer from 1 to 100,000; and
each $L^2$ is independently selected from the group consisting of a terminal group, a π conjugated segment, a linker and a linked specific binding member.

5. The dye according to claim 4, wherein at least one of $B^1$, $B^2$, $M^1$ and $M^2$ comprises -$L^1$-$C^1$, wherein $L^1$ is an optional linker and $C^1$ is the acceptor chromophore.

6. The dye according to claim 4, wherein the dye is described by the formula (III):

(III)

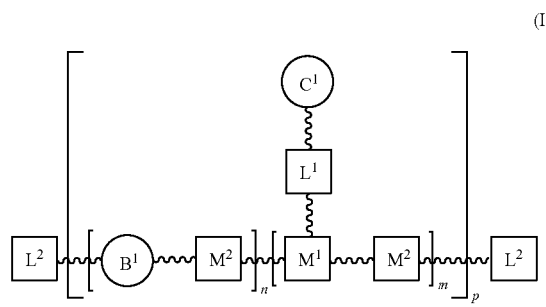

wherein each L¹ is an optional linker and each C¹ is an acceptor chromophore.

7. The dye according to claim 4, wherein the dye is described by the formula (IV):

(IV)

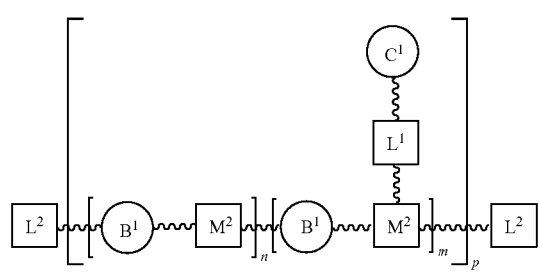

wherein each L¹ is an optional linker and each C¹ is an acceptor chromophore.

8. The dye according to claim 4, wherein the dye is described by the formula (V):

(V)

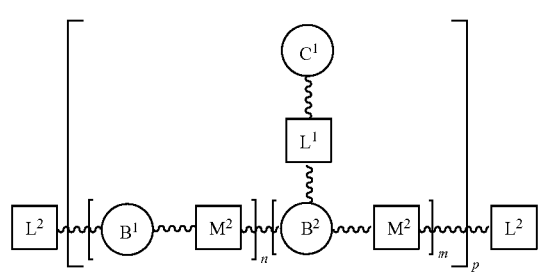

wherein each L² is an optional linker and each C¹ is an acceptor chromophore.

9. The dye according to claim 4, wherein the dye is described by the formula (VI):

(VI)

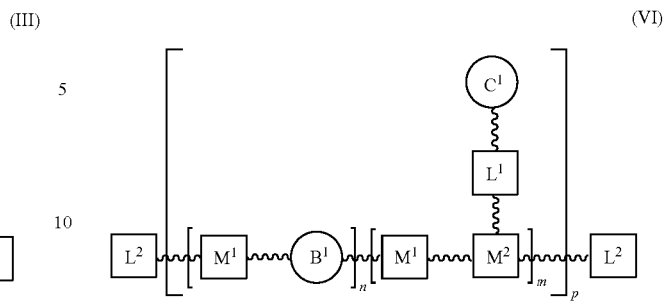

wherein each L¹ is an optional linker and each C¹ is an acceptor chromophore.

10. The dye according to claim 4, wherein $B^1$ and $B^2$ are each independently described by the following structure:

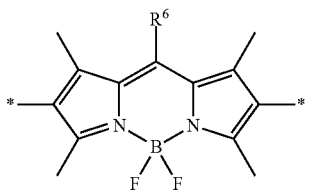

wherein $R^6$ is an aryl or a heteroaryl, optionally substituted with one or more water solubilizing groups.

11. The dye according to claim 4, wherein at least one $L^2$ is -$L^3$-Z where $L^3$ is a linker and Z is a specific binding member.

12. The dye according to claim 4, wherein each $M^1$ and $M^2$ are each independently described by the following structure:

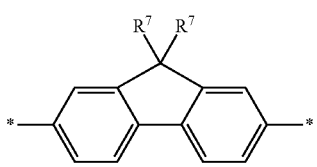

wherein:

each $R^7$ is independently selected from the group consisting of an alkyl, a substituted alkyl, an aralkyl, a substituted aralkyl, a PEG moiety and -$L^1$-$C^1$.

13. The dye according to claim 4, wherein:

$M^1$ is described by the following structure:

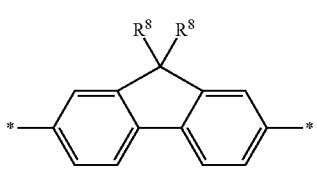

wherein each $R^8$ is a substituted aralkyl that comprises a water solubilizing group; and $M^2$ is described by the following structure:

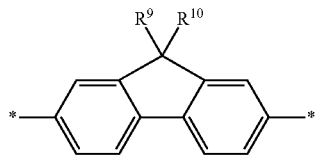

wherein $R^9$ is a substituted alkyl that comprises a water solubilizing group, and $R^{19}$ is -$L^1$-$C^1$.

14. A labelled specific binding member, comprising:
a polymeric tandem dye comprising:
   a water soluble light harvesting BODIPY unit-comprising multichromophore;
   an acceptor chromophore covalently linked to the multichromophore in energy-receiving proximity therewith; and
   a specific binding member covalently linked to the multichromophore.

15. The labelled specific binding member according to claim 14, wherein the multichromophore comprises a BODIPY-comprising conjugated segment described by formula (I):

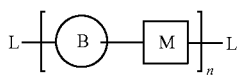

wherein:
B is a BODIPY unit;
M is a π conjugated co-monomer;
each L is independently selected from the group consisting of a terminal group, a π conjugated segment, a linker and a linked specific binding member; and
n is an integer of 1 to 100,000.

16. The labelled specific binding member according to claim 14, wherein the BODIPY unit is described by the structure:

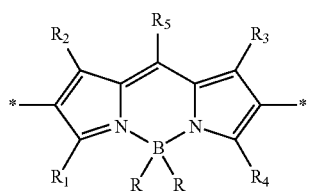

wherein:
$R^1$, $R^2$, $R^3$ and $R^4$ are each independently selected from H, an alkyl and a substituted alkyl;
$R^5$ is selected from the group consisting of an alkyl, a substituted alkyl, an aryl, a substituted aryl, a heteroaryl and a substituted heteroaryl, wherein $R^5$ is optionally substituted with a water solubilizing group; and
each R is selected from the group consisting of F, OH, H, alkyl, substituted alkyl, aryl, substituted aryl, heteroaryl, substituted heteroaryl, alkoxy, substituted alkoxy, alkynyl and substituted alkynyl.

17. The labelled specific binding member according to claim 14, wherein the multichromophore is described by the formula (II):

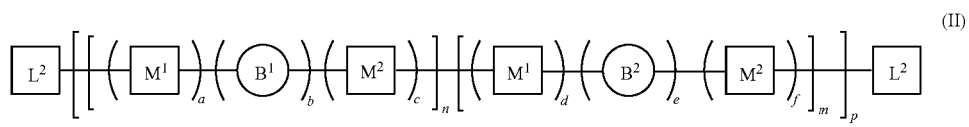

wherein:
$B^1$ and $B^2$ are each independently a BODIPY unit;
each $M^1$ and each $M^2$ are independently a π conjugated co-monomer;
a, b, c, d, e and f are each independently 0, 1 or 2, wherein b+e≥1;
n and m are independently 0 to 100,000, wherein n+m≥1; and
one $L^2$ group is a terminal group ($G^1$) and the other $L^2$ group is a linked specific binding member.

18. The labelled specific binding member according to claim 17, wherein at least one of $B^1$, $B^2$, $M^1$ and $M^2$ comprises -$L^1$-$C^1$, wherein L' is an optional linker and $C^1$ is the acceptor chromophore.

19. The labelled specific binding member according to claim 14, wherein the acceptor chromophore is selected from the group consisting of a cyanine dye, a xanthene dye, a coumarin dye, a thiazine dye and an acridine dye.

20. A method of evaluating a sample for the presence of a target analyte, the method comprising:
(a) contacting the sample with a polymeric tandem dye conjugate that specifically binds the target analyte to produce a labelling composition contacted sample, wherein the polymeric tandem dye conjugate comprises:
   (i) a light harvesting BODIPY unit-comprising multichromophore;
   (ii) an acceptor chromophore covalently linked to the multichromophore in energy-receiving proximity therewith; and
   (iii) a specific binding member; and
(b) assaying the labelling composition contacted sample for the presence of a polymeric tandem dye conjugate-target analyte binding complex to evaluate whether the target analyte is present in the sample.

* * * * *